United States Patent
Sim

(10) Patent No.: US 10,588,730 B2
(45) Date of Patent: Mar. 17, 2020

(54) MESH ASSEMBLY AND MANUFACTURING METHOD THEREOF

(71) Applicant: Kil Sub Sim, Seongnam-si (KR)

(72) Inventor: Kil Sub Sim, Seongnam-si (KR)

( * ) Notice: Subject to any disclaimer, the term of this patent is extended or adjusted under 35 U.S.C. 154(b) by 994 days.

(21) Appl. No.: 14/954,152

(22) Filed: Nov. 30, 2015

(65) Prior Publication Data

US 2016/0256252 A1 Sep. 8, 2016

(30) Foreign Application Priority Data

Mar. 5, 2015 (KR) .................. 10-2015-0030964

(51) Int. Cl.
| | |
|---|---|
| A61F 2/02 | (2006.01) |
| A61B 17/03 | (2006.01) |
| A61F 2/00 | (2006.01) |
| A61B 17/06 | (2006.01) |
| A61B 17/00 | (2006.01) |

(52) U.S. Cl.
CPC ...... *A61F 2/0059* (2013.01); *A61B 17/06166* (2013.01); *A61F 2/0045* (2013.01); *A61B 2017/00792* (2013.01); *A61B 2017/00805* (2013.01); *A61B 2017/06176* (2013.01); *A61F 2/0063* (2013.01); *A61F 2220/005* (2013.01); *A61F 2220/0016* (2013.01); *A61F 2220/0058* (2013.01); *A61F 2220/0075* (2013.01); *A61F 2230/0069* (2013.01); *A61F 2240/001* (2013.01)

(58) Field of Classification Search
CPC .... A61F 2/0063; A61F 2/0059; A61F 2/0045; A61F 2220/0016; A61F 2220/0075; A61B 17/06166; A61B 2017/06176
See application file for complete search history.

(56) References Cited

U.S. PATENT DOCUMENTS

| | | | |
|---|---|---|---|
| 2011/0130774 A1* | 6/2011 | Criscuolo ............. | A61F 2/0063 606/151 |
| 2012/0277770 A1* | 11/2012 | Fenton ............. | A61B 17/06166 606/151 |

FOREIGN PATENT DOCUMENTS

| | | |
|---|---|---|
| KR | 100577292 | 5/2006 |
| KR | 200431723 | 11/2006 |
| KR | 100961679 | 6/2010 |
| KR | 1020100058650 | 6/2010 |
| KR | 1020110126118 | 11/2011 |
| KR | 101155817 | 6/2012 |
| KR | 101318309 | 10/2013 |
| KR | 101337465 | 12/2013 |
| KR | 1020140030648 | 3/2014 |
| KR | 101432500 | 8/2014 |
| KR | 101182337 | 9/2015 |

* cited by examiner

*Primary Examiner* — Katherine M Rodjom
(74) *Attorney, Agent, or Firm* — Eunyoung Lee

(57) ABSTRACT

Provided is a mesh assembly inserted to a soft tissue or a human tissue for lifting the soft tissue, the mesh assembly including: a mesh member inserted into the soft tissue or human tissue and supporting the tissue; a fixed member provided at the mesh member and adopted to increase a coupling force in the soft tissue or the body; and a hook member formed on an upper surface or a lower surface or both of the fixed member to protrude in a diagonal direction, so that fixation of the soft tissue or human tissue can be firmly conducted, thereby allowing the soft tissue and the like to be fixed at a normal position without undergoing an influence by shaking or an external shock.

10 Claims, 28 Drawing Sheets

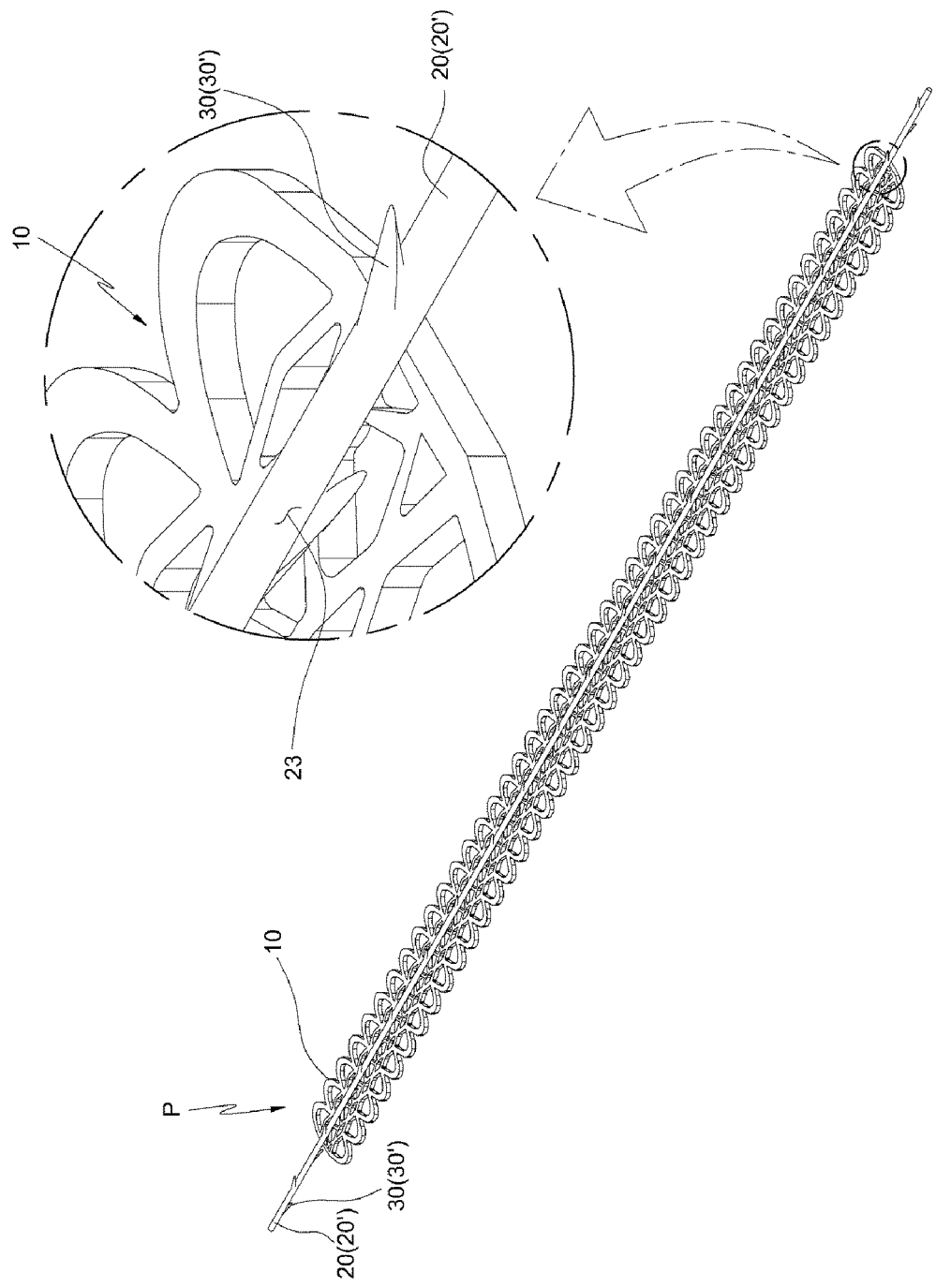

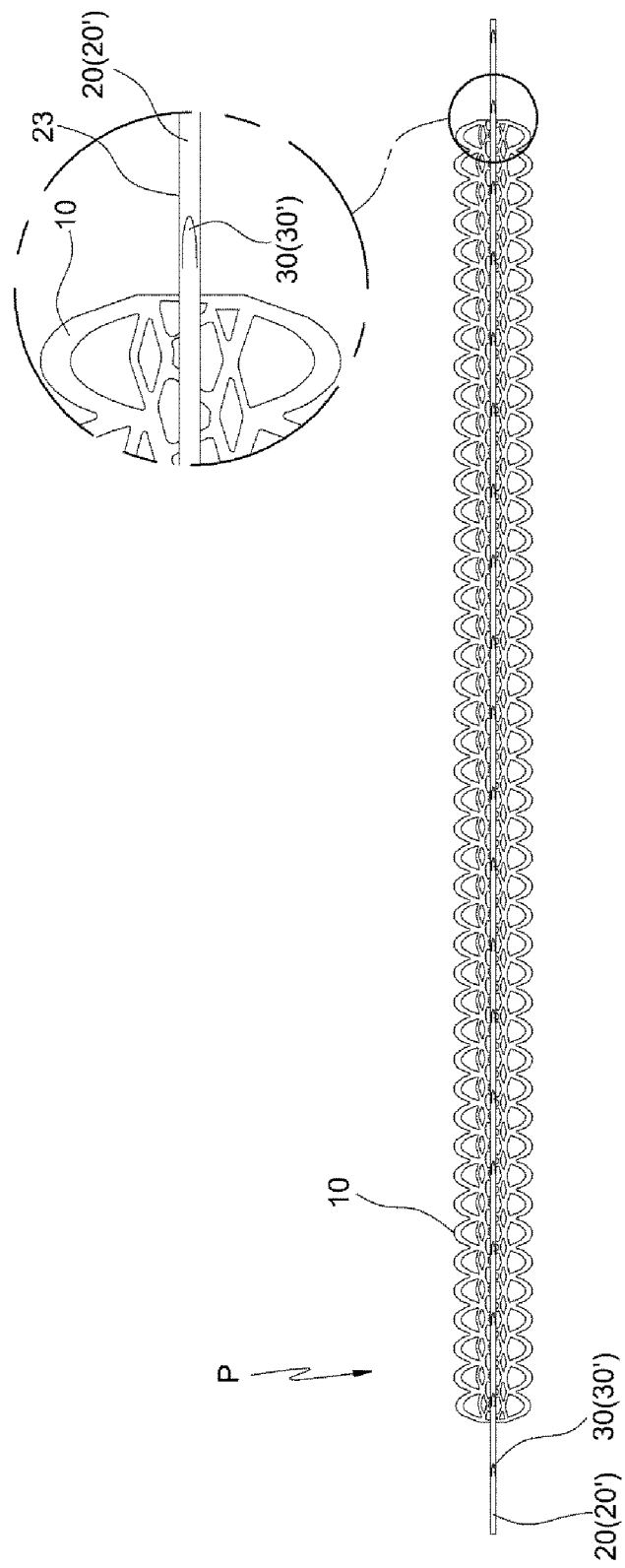

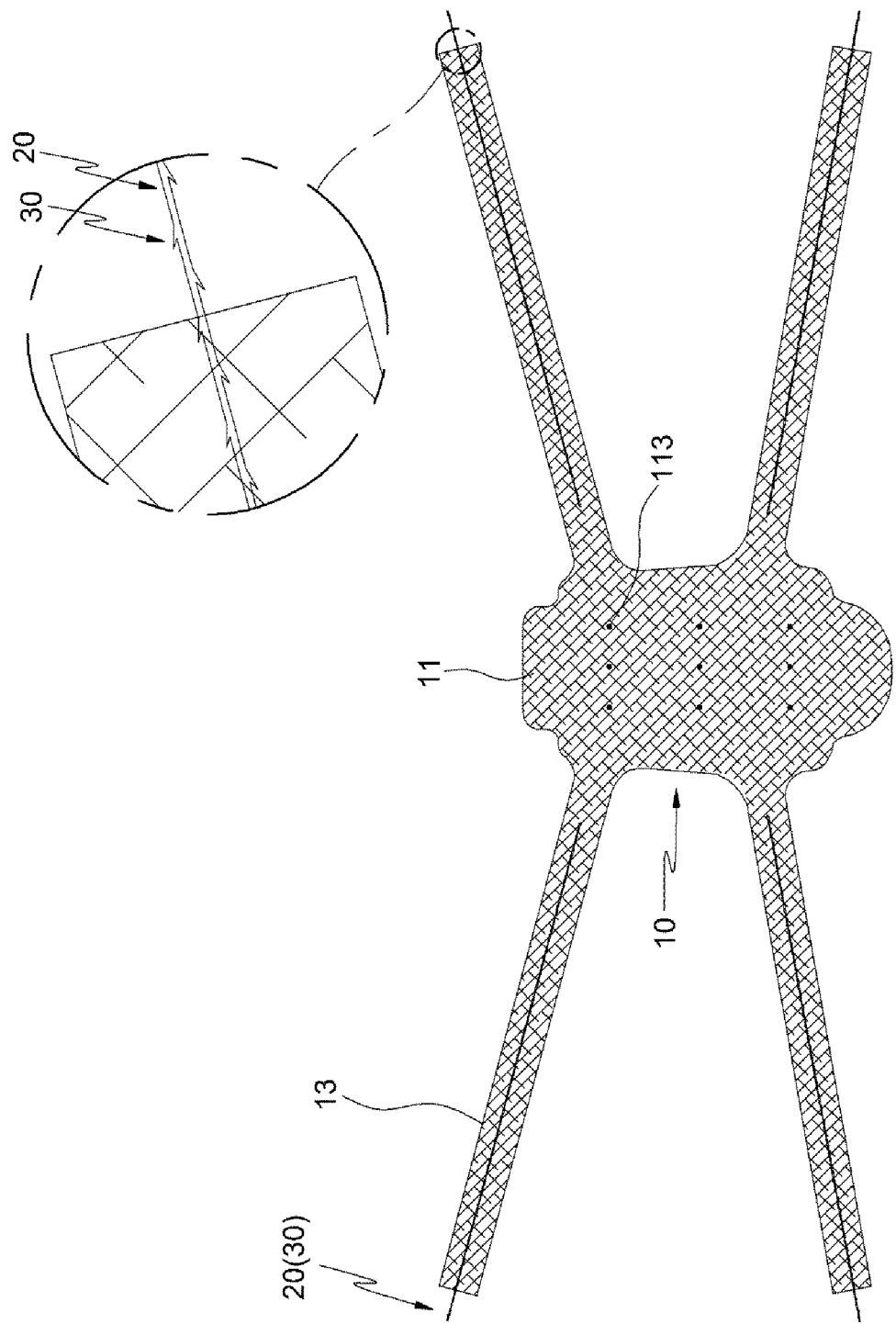

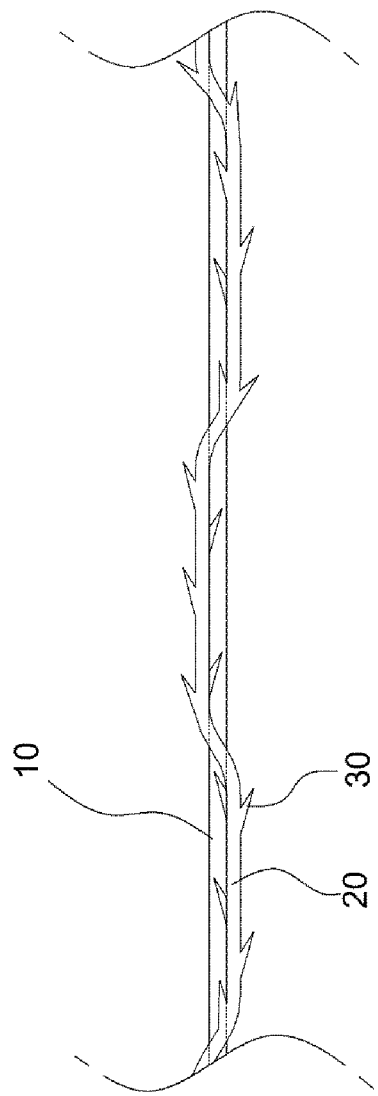

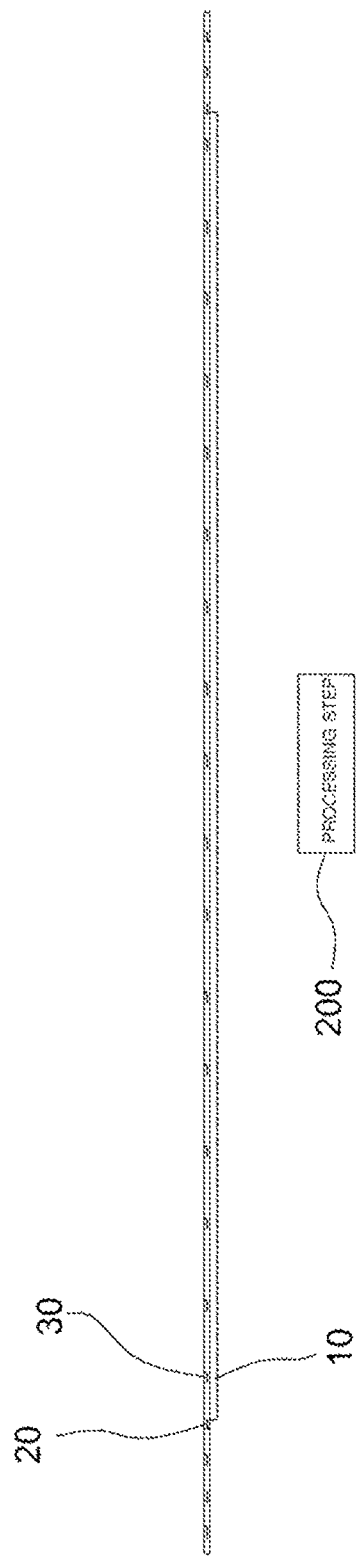

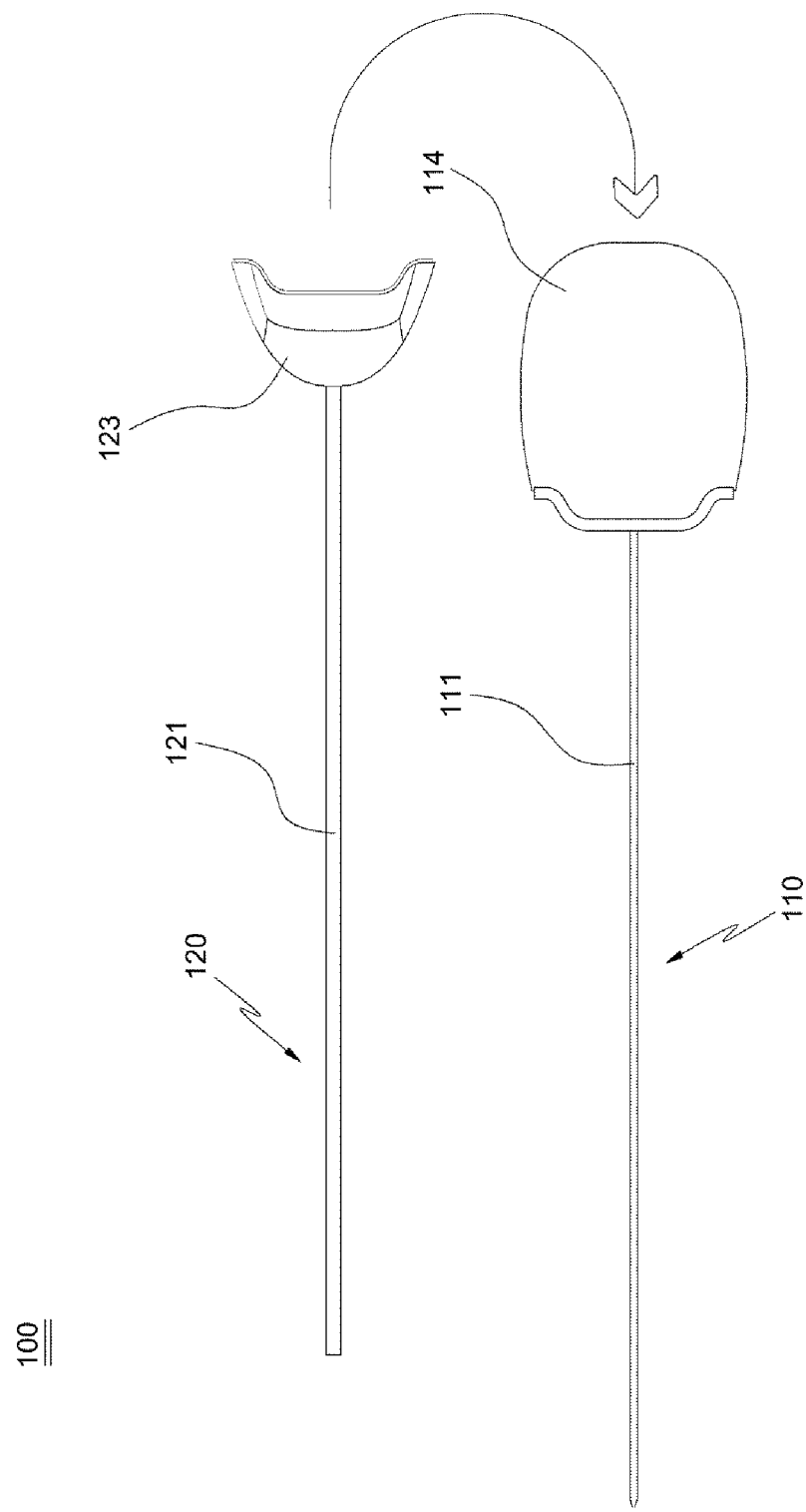

MESH ASSEMBLY AND MANUFACTURING METHOD THEREOF

BACKGROUND OF THE INVENTION

Field of the Invention

The present invention relates generally to meshes inserted into soft tissues or human tissues in order to lift the soft tissues or human tissues. More particularly, the present invention relates to a mesh assembly and a method of manufacturing the mesh assembly, the mesh assembly including: a mesh inserted into a soft tissue or a human tissue and adopted to support the soft tissue or human tissue; a fixed member provided at the mesh and adopted to increase a binding force of the soft tissue or human tissue; and a hook member formed on an upper surface or a lower surface or both of the fixed member to protrude in a diagonal direction, so that fixation of the soft tissue or human tissue can be firmly conducted, thereby allowing the soft tissue or the like to be fixed at a normal position without undergoing an influence by shaking or external shock.

Description of the Related Art

An example of a conventional art includes Korean Patent No. 10-1337465 entitled [Mesh Assembly for Plastic Surgery]. This conventional art presents a mesh assembly for plastic surgery that can smooth out wrinkles in the skin by lifting loose skin in a state of being inserted into the skin of the body, the mesh assembly including: a net body inserted into the skin of the body and entirely or partially adhered to the skin tissue, the net body entirely forming a two-dimensional plane and having a through hole; and a controller having a long thread form and coupled to the net body by passing through the through hole so as to pull the net body.

However, despite the fact that the conventional art can increase adhesion power with the skin tissue by forming the net body inserted into the skin, it is problematic in that since the adhesive force becomes weak due to shaking or external shock, the mesh assembly may be separated from the skin tissue.

Another example of a conventional art includes Korean Utility Model No. 20-0431723 entitled [Mesh for Surgical Operation of Urinary Incontinence].

The conventional art presents a mesh for surgical operation of urinary incontinence, including: a mesh portion in which a plurality of meshes with a regular width and formed in a net form is connected to each other; and a plurality of connection portions formed on both surfaces of each mesh and having separation strings, the separation strings being adopted to combine each mesh by connecting respective both surfaces of the plurality of meshes to each other and to separate each mesh from each other by pulling the separation strings to untie the separation strings, whereby knots are formed so that the meshes are separated from the connections portions by pulling the separations strings positioned at the connection portions of each mesh to untie the separation strings.

However, despite the fact that the conventional art, which relates to the meshes inserted into the skin and adhered to the skin tissue and the like, may increase adhesion power by improving a contact area, it may be problematic in that the meshes deviate from the position of a part targeted for the procedure due to shaking or external shock before the meshes adhere to the tissue.

Furthermore, a further example of a conventional art includes Korean Patent Laid-Open Publication No. 10-2011-0126118 entitled [Implant For Pelvic Organ Prolapse Repair].

The conventional art presents an implant for pelvic organ prolapse repair, wherein the implant is intended to repair prolapses of various pelvic organs including vaginal vault prolapse, and includes: a first flap comprising a dual density mesh formed of a first and second filament; a second flap comprising a single density mesh formed of the first filament, and a third flap comprising a single density mesh formed of the second filament. The first, second, and third flaps can share a common intersection that can form an arc. The implant can be formed by knitting a uniform piece of mesh and the arc.

However, the conventional art is intended to repair prolapses of pelvic organs by overlappingly arranging the filaments having the plurality of meshes and is problematic in that the implant is not fixed to a correct position targeted for the procedure due to shaking or external shock before the first and second filaments adhere to the skin tissue.

Yet another example of a conventional art includes Korean Patent No. 10-0577292 entitled [Method of Manufacturing Artificial Insertion for Plastic Surgery in Sinking Site]. The conventional art presents a method of manufacturing an artificial insertion for plastic surgery in a sinking site, the method including: making a lower wound model frame by measuring a wound shape in a sinking site of a patient with plaster or silicon; coating the sinking site of the lower wound model frame with wax and paraffin; making an upper wound model frame corresponding to the lower wound model frame; forming a sinking portion in the lower wound model frame by removing the wax and paraffin after making the upper and lower wound model frames; and solidifying the upper wound model frame and the lower wound model frame.

In addition, still another example of a conventional art includes Korean Patent No. 10-0961679 [Method of Manufacturing Artificial Insertion for Plastic Surgery in Sinking Site Using Liquid Silicon].

The conventional art presents a method of manufacturing an artificial insertion for plastic surgery in a sinking site using liquid silicon, which can accurately repair the sinking site while completely implementing a tissue (skin) and shape property and hardness property for the sinking site of a patient. Furthermore, the method can prevent bubbles from being generated during a solidifying process of the liquid silicon by using a defoaming process, can increase quality of the product, and can improve workability by introducing a cell tissue of the patient to a pre-molded hole during growth of the cell tissue after inserting the manufactured artificial insertion so that an implant can be accurately positioned at the sinking site, thereby reducing a secondary man-hours required when using a separate fixing plate or fixing thread.

However, the conventional art, which is intended to manufacture the artificial insertion to be inserted into the sinking site of the patient, may cause inflammation by rejection with the human tissue because the artificial insertion is molded using the liquid silicon. In addition, it is problematic in that a recipient can acutely sense a foreign object inside his or her body; costs are increased because different artificial insertions should be manufactured according to a sinking level; and it takes a long time to mold the artificial insertion.

SUMMARY OF THE INVENTION

Accordingly, the present invention has been made keeping in mind the above problems occurring in the related art, and an object of the present invention is to provide a mesh assembly that can be fixed at a normal position of a part targeted for a procedure by including a mesh supporting a tissue for the procedure for lifting the tissue or the like, a fixed member provided at the mesh and adopted to fix the mesh and the soft tissue, and a hook member adopted to increase adhesion power.

Another object of the present invention is to provide a mesh assembly that is configured such that the fixed member is formed with a thread that is harmless to humans so that a production process can be simplified, and the hook member is composed of protrusions formed on an upper surface or a lower surface or both of the fixed member so that the protrusions can maximize adhesion power with the tissue at an upper surface and a lower surface of the mesh and can facilitate firm fixation of the mesh and the tissue.

A further object of the present invention is to provide a mesh assembly that is configured such that the protrusions are maintained obliquely from the fixed member to one direction so as to facilitate firm fixation with a tissue, and grooves having a size corresponding to 10% or more and 40% or less of the diameter of a thread are formed in the fixed member so that the fixed member can be prevented from being cut due to the grooves having an excessive size or the protrusions can be prevented from failing to protrude due to the grooves having a small size.

Furthermore, yet another object of the present invention is to provide a mesh assembly that can control a force supporting a tissue by forming one or more fixed members in a mesh according to a size of the tissue or a procedural method.

In addition, still another object of the present invention is to provide a method of manufacturing a mesh assembly, including: an adhesion step of adhering a fixed member in a mesh; and a processing step of forming grooves in the fixed member subjected to the adhesion step to form a hook member, the steps being sequentially conducted, so that the hook member can be formed at an accurate position corresponding to an upper surface or a lower surface or both of the fixed member, and the hook member can be formed by the processing step and the fixed member can be fixed to the mesh by the adhesion step.

Moreover, still another object of the present invention is to provide a mesh assembly that is configured such that a mesh in which both a first thread having a hook member and a second thread having no hook member are interpolated is provided so that a first space part and a second space part are formed in the mesh member, thereby enabling expansion of a subcutaneous tissue.

In addition, still another object of the present invention is to provide a mesh assembly that is configured such that an outer circumferential surface of the second thread is composed of a flat portion so that only the second thread in the human tissue is separated from the mesh, thereby making firm knots after a procedure, and the hook member of the first thread protrudes to the outside of the mesh so as to increase a frictional force with a human tissue in contact so that the mesh can be accurately fixed to a procedure position after lifting of the soft tissue and the procedure.

In order to achieve the above objects, according to one aspect of the present invention, there is provided a mesh assembly, including: a mesh; a fixed member provided at the mesh; and a hook member formed on an outer surface of the fixed member, wherein the fixed member is composed of a thread, and the hook member is composed of a plurality of protrusions formed on an upper surface or a lower surface of both of the fixed member, the protrusions protruding from the fixed member to one direction.

In addition, according to another aspect of the present invention, a mesh assembly includes: a first thread having a hook member on an outer surface thereof; a second thread positioned at a rear end of the first thread; and a mesh having a space portion in which both the first thread and the second thread are interpolated, and formed to surround both the first thread and the second thread, wherein the space portion comprises a first space part in which the first thread is interpolated, and a second space part in which the second thread is interpolated; an outer surface of the second thread is composed of a flat portion; a rear end of the second thread and a rear end of the mesh are fixed to each other; and a fixing portion, which may be cut, is formed so that the second thread is separated from the second space portion by cutting.

As described above, the mesh assembly according to the present invention includes the mesh supporting the tissue for the procedure for lifting the tissue or the like, and the fixed member provided at the mesh and having a hook member so that adhesion power with the tissue in the body can be improved by the hook member, and the mesh can be accurately fixed to a procedure position. In addition, since the fixed member is formed with a thread that is harmless to humans, the occurrence of complications can be minimized and a production cost can be reduced.

Furthermore, since the hook member is composed of a plurality of protrusions formed on an upper surface or a lower surface or both of the fixed member, the protrusions protruding from the fixed member to one direction, a supporting force in tissue can be secured, and the mesh can firmly support the tissue.

Since one or more fixed members are provided at the mesh, a stronger supporting force can be secured according to a size of the tissue or an escape level.

Furthermore, the adhesion step of adhering the fixed member to the mesh member and the process step of forming grooves in the fixed member subjected to the adhesion step to form the hook member are sequentially conducted so that the hook member can be accurately formed at an upper position or a lower position of the fixed member, and the hook member can be prevented from being warped or being damaged by adhesion of the fixed member and the mesh.

Moreover, according to some embodiments, thanks to the mesh that forms a space portion in which both the first thread having the hook member and the second thread having the outer surface composed of the flat portion rather than the hook member are interpolated, the loose skin of a patient in a subcutaneous tissue can be restored, and wrinkled parts can be selectively provided with a volume.

Since the mesh is formed in a cylindrical shape, it is effective to restore the elasticity of skin due to a tissue ingrowth phenomenon (which means that a tissue grows gradually in the mesh).

In addition, since a thread is used, the occurrence of inflammation caused by rejection with a human tissue can be more effectively prevented compared to the case in which a conventional implant made of silicon is inserted.

Thanks to the hook member formed on the first thread, an absorptive force with the human tissue can be enhanced, and the mesh can be accurately inserted into a therapy site, thereby increasing stability and a success rate of procedures.

Also, since the second thread is separated from the mesh, when a knot is made for a part protruding from a human tissue for fixation after a procedure, the part is tied with the soft mesh in order to solve an existing problem that when the part is tied with a thread, the thread is easily snapped, thereby enabling firm fixation.

BRIEF DESCRIPTION OF THE DRAWINGS

The above and other objects, features and other advantages of the present invention will be more clearly understood from the following detailed description when taken in conjunction with the accompanying drawings, in which:

FIG. 1 is perspective view of a mesh assembly according to a first embodiment of the present invention;

FIGS. 2A and 2B are plane view and a side view of the mesh assembly according to the first embodiment of the present invention;

FIG. 4 illustrates a mesh assembly according to a third embodiment of the present invention;

FIGS. 5A and 5B illustrate a mesh assembly according to a fourth embodiment of the present invention;

FIGS. 7A to 7C are process views showing a method of manufacturing a mesh assembly according to the present invention;

FIG. 16 is a perspective view showing a cannula for a procedure using the mesh assembly according to the present invention.

DETAILED DESCRIPTION OF THE INVENTION

Figure 2B:
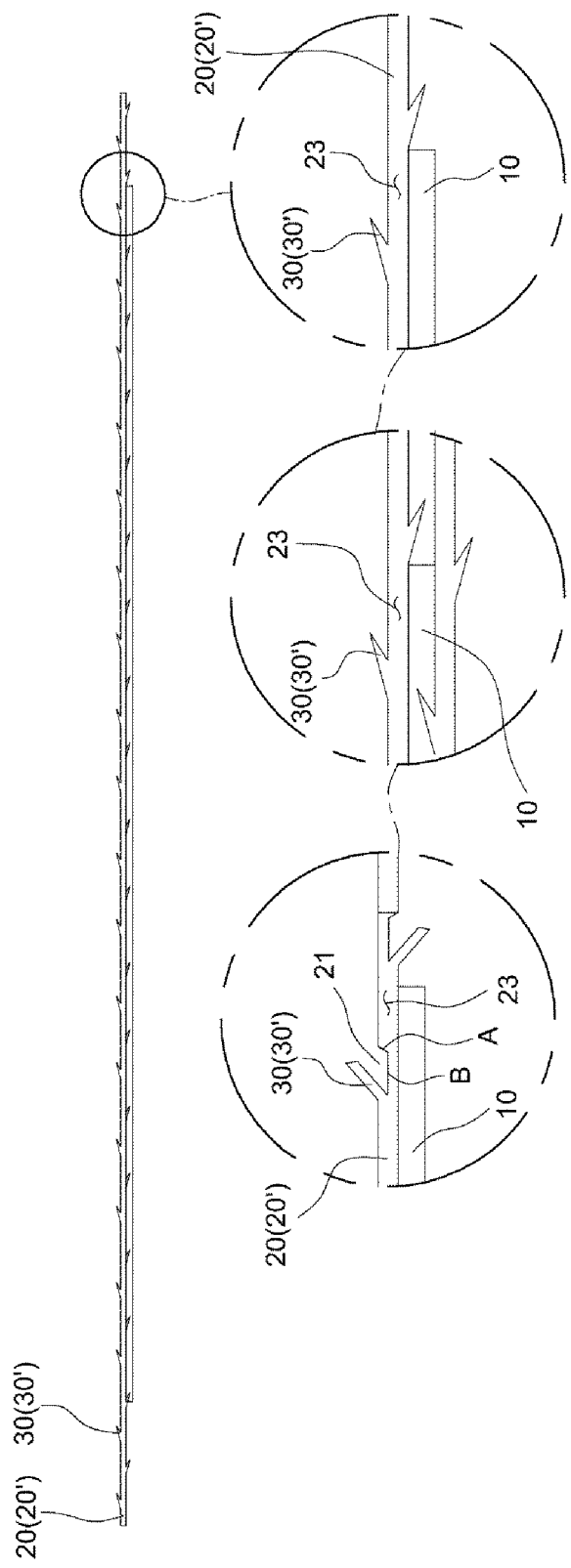

The present invention will now be described in detail based on aspects (or embodiments). The present invention may, however, be embodied in many different forms and should not be construed as being limited to only the embodiments set forth herein, but should be construed as covering modifications, equivalents or alternatives falling within ideas and technical scopes of the present invention.

In the figures, like reference numerals, particularly, reference numerals having the same last two digits or the same last two digits and letters refer to like elements having like functions throughout, and unless the context clearly indicates otherwise, elements referred to by reference numerals of the drawings should be understood based on this standard.

Also, for convenience of understanding of the elements, in the figures, sizes or thicknesses may be exaggerated to be large (or thick), may be expressed to be small (or thin) or may be simplified for clarity of illustration, but due to this, the protective scope of the present invention should not be interpreted narrowly.

The terminology used herein is for the purpose of describing particular aspects (or embodiments) only and is not intended to be limiting of the present invention. As used herein, the singular forms are intended to include the plural forms as well, unless the context clearly indicates otherwise. It will be further understood that the terms "comprises," "comprising,", "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which the present invention belongs. It will be further understood that terms used herein should be interpreted as having a meaning that is consistent with their meaning in the context of this specification and the relevant art and will not be interpreted in an idealized or overly formal sense unless expressly so defined herein.

First, as illustrated in FIGS. 1, 2A and 2B, a medical mesh assembly P according to the present invention includes: a mesh 10; a fixed member 20 provided with the mesh 10; and a hook member 30.

As illustrated in FIGS. 1, 2A and 2B, the mesh assembly according to the present invention is configured such that the fixed member 20 is further provided with the mesh supporting a soft tissue, and the hook member 30 adopted to give a supporting force to the mesh 10 for enabling firm fixation by increasing adhesion power with the soft tissue is further included on an outer surface of the fixed member 20, the hook member.

FIGS. 1, 2A and 2B illustrate a mesh assembly according to a first embodiment of the present invention.

In detail, the mesh 10 may be made of a material that is harmless to humans, and more specifically, the mesh 10 may be molded with polypropylene that is harmless to humans. According to circumstances, the mesh may be made of a soluble material such as gold, stainless, polydioxanone, PGA, PGLA, PDO and the like, which can melt in human bodies. The fixed member 20 connected to the mesh 10 may be also made of a soluble material.

Also, the mesh 10 may function to surround and support the tissue and may be formed in a mesh structure so as to uniformly support the tissue by increasing a contact area with the tissue. In order to prevent the mesh 10 from shaking when a procedure is carried out, as illustrated in FIG. 4, the mesh assembly may further include a binding portion 113 adopted to stitch the mesh 10 and an organ using thread 20' or the like.

Returning to FIGS. 2A and 2B again, the fixed member is further provided at the mesh 10. The fixed member 20 is composed of the thread 20', and the hook member 30 is further provided on the outer surface of the fixed member 20.

More specifically, the fixed member 20 may be provided at the mesh 10 such that the fixed member 20 and the mesh are connected to each other using an adhesive or the like that is harmless to humans, or by melting the mesh or the fixed member 20.

The fixed member 20 is composed of the thread 20', and the hook member 30 is further formed on an outer circumferential surface of the thread 20'. In addition, the hook member 30 is composed of a plurality of protrusions 30' that is formed at an upper part or a lower part or both of the fixed member 20. The protrusions 30' are characterized by slantingly protruding from the fixed member 20 to one direction.

In detail greater, as illustrated in each of alternate long and short dash lines of FIGS. 2A and 2B, the protrusions 30' formed on the outer circumferential surface of the thread 20' of the fixed member 20 may be formed at an upper part or a lower part or both along the outer circumferential surface of the thread 20' of the fixed member 20, may be adhered to the thread 20' through a separate process, or may be formed by making cuts in the thread 20'. When the cuts are made in a surface of the thread 20', grooves 21 having a predetermined depth are formed, and a part of the thread 20' adjacent to the groove 21 is exposed to the outside so that the protrusions 30' are naturally formed. When this method is used, the protruding protrusions 30' may be formed without the use of an additional material except for the thread 20'.

In addition, the groove 21 may have a depth corresponding to 10% or more and 40% or less of a diameter of the thread 20'. When the depth of the groove 21 is greater than 40% of the diameter of the thread 20', the thread 20' may snap. When the depth of the groove 21 is smaller than 10% of the diameter of the thread 20', a fixing effect of the body tissue may be reduced because the protrusions 30' fail to sufficiently protrude.

In addition, the protrusions 30' may be formed at a position opposite to both sides of the thread 20'. However, in such a case, since the thread 20' has risk of snapping due to the groove 21, the protrusions 30' may be alternately formed, in a zigzag form, on an upper surface and a lower surface of the thread 20'.

Furthermore, in the case where the groove 21 is formed in the thread 20', a diagonal line portion A is formed to be oblique to the thread 20' by diagonally making cuts in the groove 21, and a straight line portion B is then formed, in the same direction as a lengthwise direction of the thread, at an end of the diagonal line A by horizontally moving the blade of a knife. Subsequently, the blade of the knife is lifted so that the protrusions 30' may naturally protrude to the outside. In such a case, a thickness of the thread is maintained so that the problem of cutting of the thread 20' due to the groove 21 can be solved.

In addition, the fixed member 20 may be formed, in a plural number, on the upper and lower surfaces of the mesh 10. This structure is intended to solve such a problem that when the fixed members 20 are connected to one surface of the mesh 10, the protrusion 30' on a surface closely attached to the mesh 10 is not exposed to the outside due to the thickness of the mesh 10. Since the fixed members 20 are formed on both the upper and lower surfaces of the mesh 10, the protrusions 30' may be formed in both directions of the medical mesh assembly according to the present invention so that binding power with the tissue can be improved.

The hook member 30, which is composed of the protrusions 30' formed on an upper surface or a lower surface or both of the fixed member 20, is provided at the fixed member 20. As the hook member 30 is formed at the upper part or the lower part or both of the fixed member 20, a flat portion 23 having no hook member 30 is formed on both sides of the fixed member 20.

Accordingly, the flat portion 23 may solve the problem of a conventional art that when the mesh 10 to which the fixed member 20 is connected is put in a soft tissue or human body, it becomes difficult to perform a procedure because a frictional force is increased due to the protrusions 30' that are irregularly formed in all directions. The flat portion 23 formed on both surfaces of the fixed member 20 allows the fixed member 20 to be more easily put in the soft tissue or human body so that time for the procedure can be reduced. In addition, the hook member 30 formed at the upper and lower positions of the fixed member 20 may allow the mesh to be firmly fixed at a regular position.

Figure 3A:
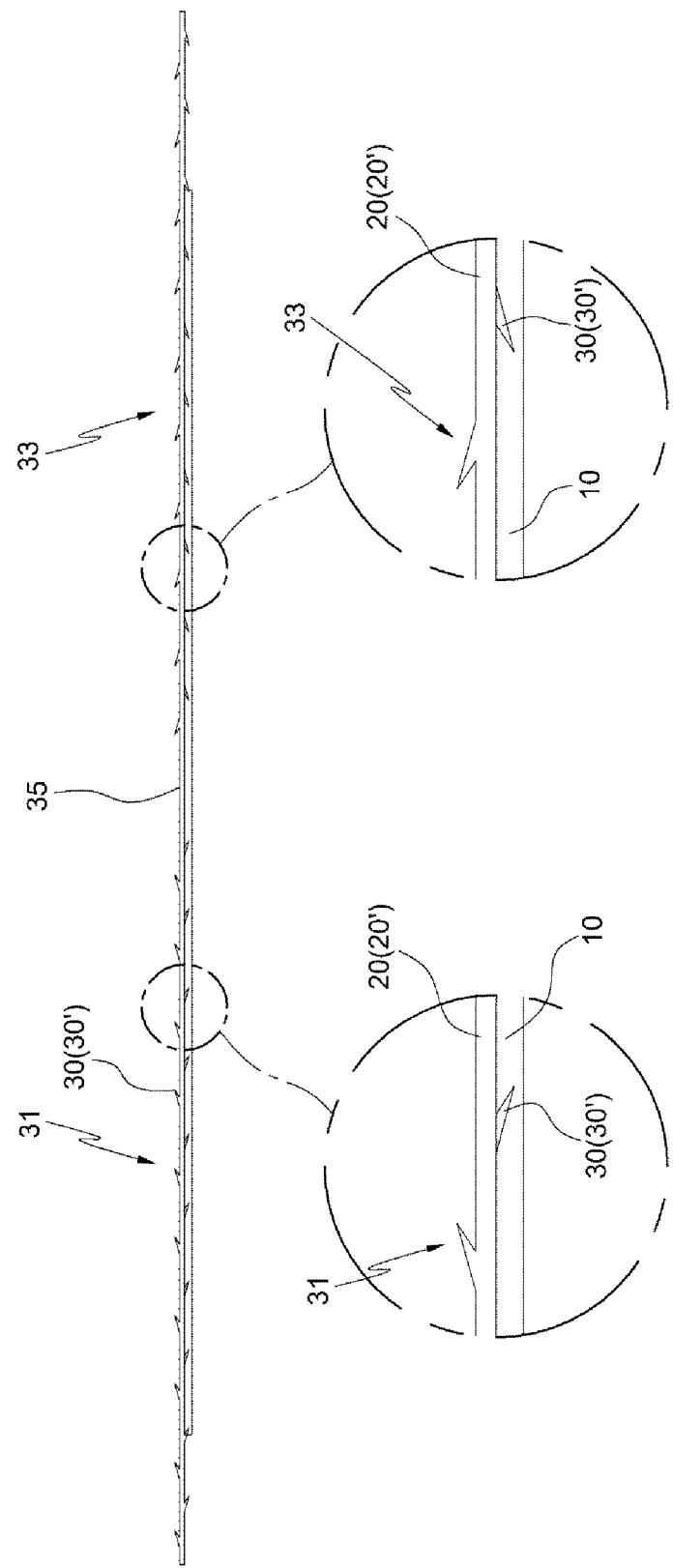
FIGS. 3A and 3B illustrate a mesh assembly according to a second embodiment of the present invention.
Figure 3B:
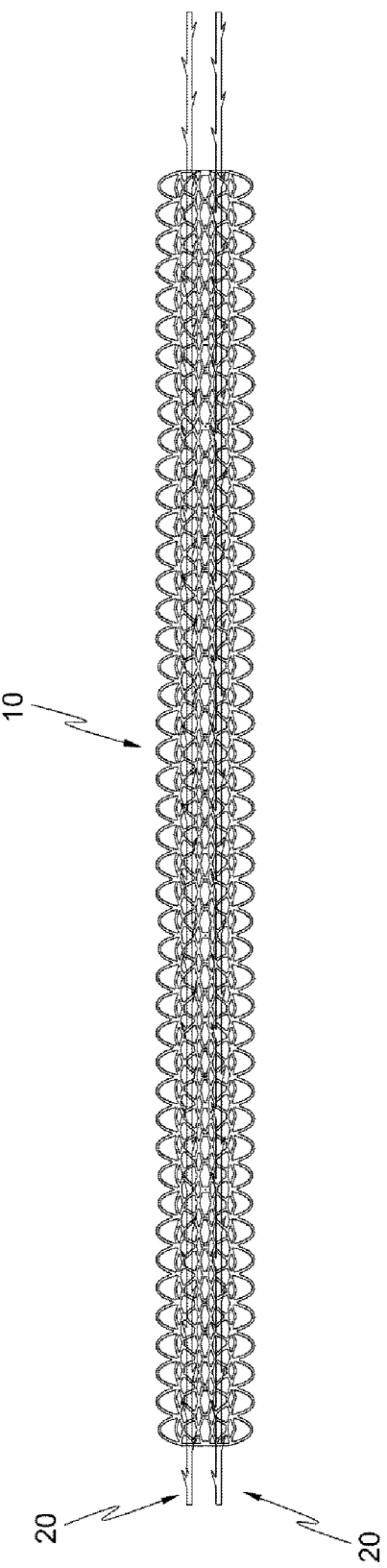

FIGS. 3A, 3B and 4 illustrate the mesh assemblies according the second and third embodiments of the present invention. The hook member 30 includes: a first hook portion 21 and a second hook portion 33 formed at the fixed member 20; a connection portion 35 formed between the first and second hook portions 31, 33. The protrusions 30' are formed in the first hook portion 31 and the second hook portion 33 to protrude diagonally in a direction of the connection portion 35.

In detail, as illustrated in FIGS. 3A, 3B and 4, the hook member 30 is formed on an outer surface of the fixed member 20. In addition, the hook member 30 includes the connection portion 35 provided in the center of the fixed member 20, and the first and second hook portions 31, 33 provided on opposite surfaces of the connection portion 35, respectively.

In such a case, the diagonally protruding protrusions 30' are formed in the first and second hook portions 31, 33. The protrusions 30' are formed to be oblique toward the connection portion 35 and are configured to face each other. Accordingly, the fixed member 20 is formed at the support portion 11 formed on the mesh 10 and supporting tissue, and a sustainment portion 13 that may be connect to the support portion 11 and may adhere to an adjacent tissue. When the hook member 30 adheres the fixed member 20 to the tissue via the protrusions 30' obliquely protruding to face each other based on the connection portion 35 provided in the center of the fixed member 20, the fixed member may be firmly fixed to the tissue by the hook member 30 having the protrusions protruding in opposite directions. Thus, since the tissue is firmly supported by the support portion 11 supporting tissue, a procedure, such as a lifting procedure of a soft tissue or the like, can be effectively carried out.

Moreover, each of the first and second hook portions 31, 33 and the connection portion may be provided in a plural number in a single mesh 10. The protrusions 30' of the first and second hook portions 31, 33 may protrude in the direction of the connection portion or a direction opposite thereto, or in different directions. The protrusions may be variously configured according to a procedural method conducted in the tissue and a procedural process.

In addition, as illustrated in FIG. 3B, one or more fixing members 20 may be further provided on the mesh 10. When the area of a tissue targeted for procedure is wide, a supporting force should be increased. To do so, at least two fixing members 20 are consequently arranged on the mesh 10, thereby increasing adhesion power between the fixed members and the tissue. Thus, a strong supporting force of the support portion 11 may be maintained so that firm fixation can be facilitated and a procedure for lifting the soft tissue in a wider area can be conducted.

Figure 5A:
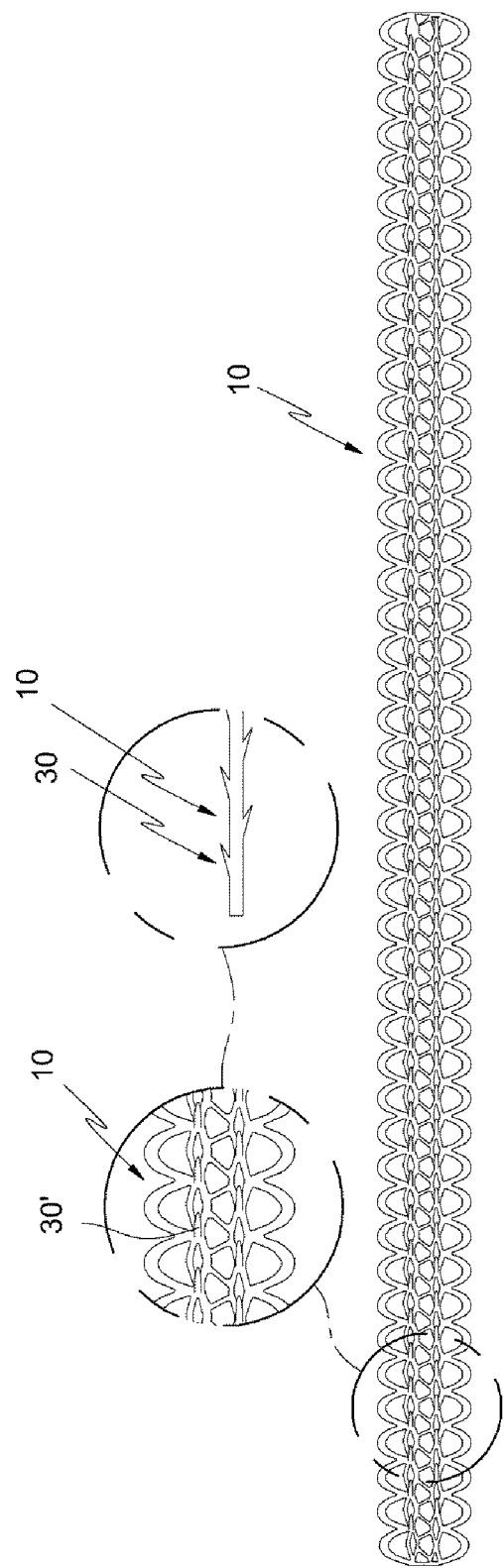

Moreover, FIGS. 5A and 5B illustrate a mesh assembly according to a fourth embodiment. The hook member 30 may be directly processed at the mesh 10, and more specifically, as illustrated in FIG. 5A, the hook member 30, which protrudes to the outside, may be directly molded, in a plural number, at the upper part or the lower part of the mesh 10. Thus, regardless of presence or absence of the fixed member 20, only the mesh 10 may be directly inserted into a site targeted for the procedure so that a production cost can be reduced, and the fixed member can be prevented from being separated from the mesh 10. Also, as illustrated in FIG. 5B, when the fixed member 20 having the hook member 30 is fixed to the mesh, the fixed member may be alternately connected to, in a zigzag form, the upper part and the lower part of the mesh. Thus, the hook member 30 may protrude from the upper and lower parts of the mesh 10 so that firm fixation can be conducted in the tissue.

Figure 6:
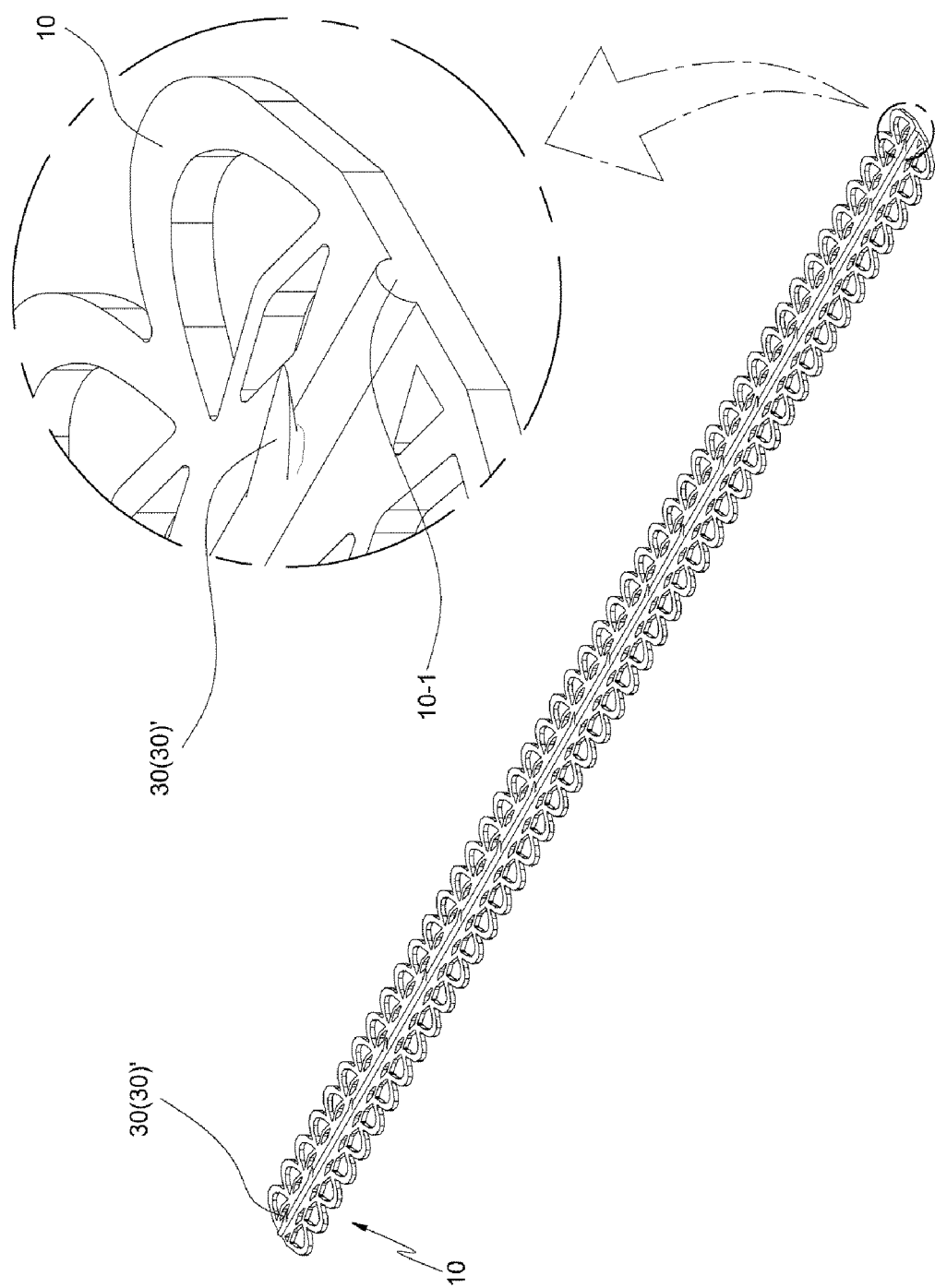
FIG. 6 illustrates a mesh assembly according to a fifth embodiment of the present invention.

Furthermore, FIG. 6 illustrates a mesh assembly according to a fifth embodiment. When the hook member 30 is directly molded on the mesh 10, the mesh has a risk of snapping due to its thinness. In order to solve this, when the mesh 10 is subjected to injection molding, a thick portion 10-1 may be formed to protrude along a central part of the mesh 10 by injection molding. Accordingly, the hook member 30 is integrally formed with the thick portion 10-1 so that the mesh 10 can be prevented from snapping. The thick portion 10-1 may be formed along the center of the mesh 10 as illustrated in FIG. 6. However, the thick portion may be formed, in a plural number, in the center or on one surface, and the scope of rights should not be limitedly construed thereto.

Figure 7A:
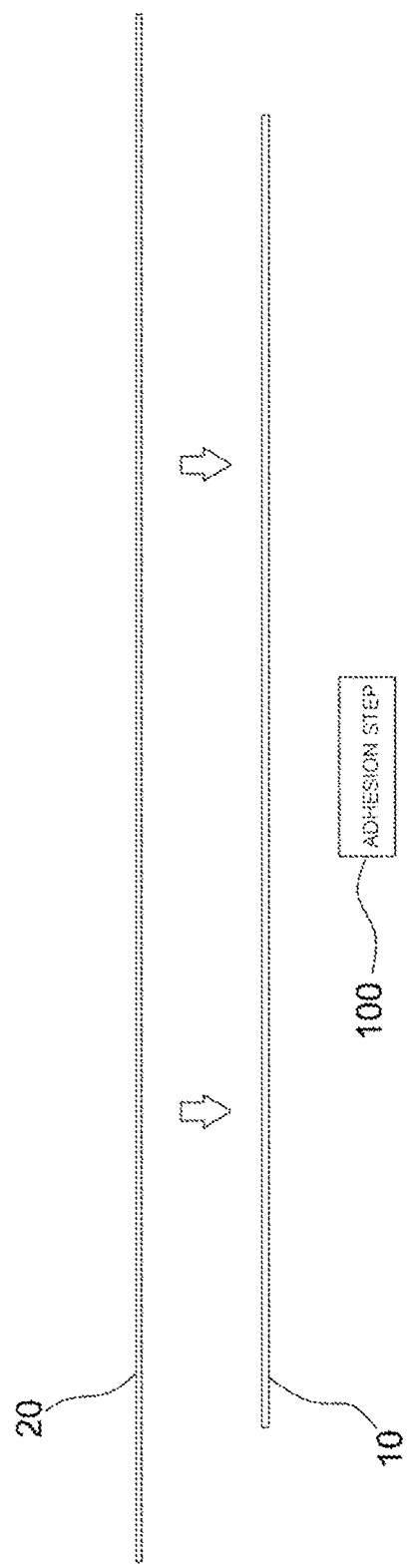
Figure 7C:
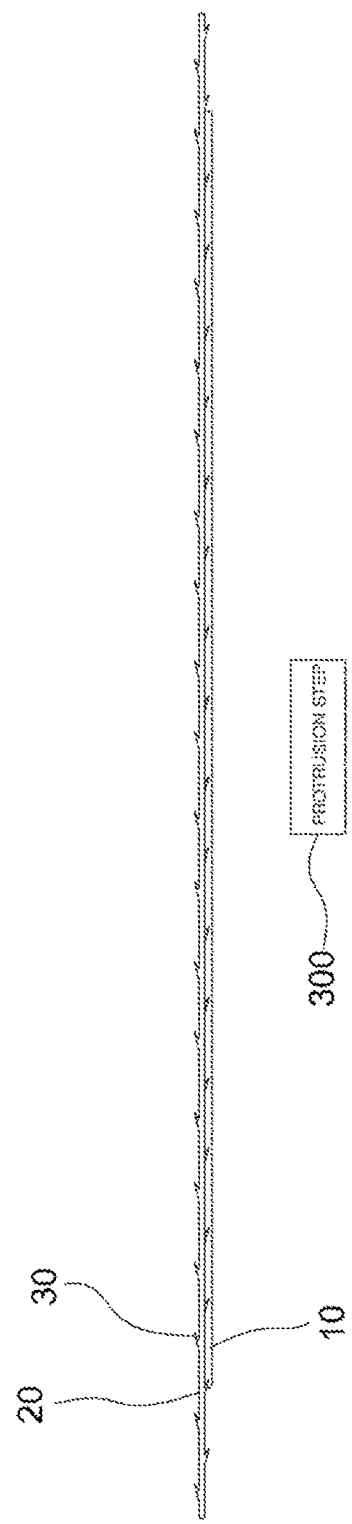

In order to manufacture the mesh assembly P according to each of the first to fifth embodiments of the present invention, as illustrated in FIGS. 7A to 7C, in order to bond the fixed member 20 to the mesh 10, the groove 21 is first formed in the fixed member 20 using a tool such as a knife and the like, and the protrusions 30' are formed by the groove 21, and thereafter, the fixed member 20 adheres to the mesh 10 again, thereby manufacturing the mesh assembly P. However, in such a case, the protrusions 30' may not be correctly formed at the upper part or the lower part or both of the fixed member 20 adhered to the mesh 10.

Accordingly, the medical mesh assembly P according to the present invention is manufactured by an adhesion step (100) of pre-adhering the fixed member to the mesh 10; and a processing step (200) of forming the hook member 30 in the fixed member 20 adhered to the mesh 10 formed by the adhesion step (100).

The processing step (200) further includes a protrusion step of causing the hook member 30 formed by the processing step (200) to protrude to the outside so that the hook member 30 formed by the processing step 200 can be molded to protrude to the outside of the fixed member 20.

Furthermore, like a conventional art, the method of forming the hook member 30 through the processing step (200) and adhering the fixed member 20 having the hook member to the mesh 10 is also included in the scope of rights of the present invention.

Also, the processing step 200 and the protrusion step 300 may be sequentially conducted. However, the processing step 200 and the protrusion step 300 may be simultaneously conducted in such a manner that the groove 21 is formed by the processing step 200, and the protrusion step 300 is performed by naturally removing the blade of a knife.

Moreover, in the case where the fixed member 20 is not provided, the adhesion step (100) may be excluded by using only the processing step (200) of forming the hook member in the mesh 10, and the protrusion step of forming the hook member 30 formed by the processing step to protrude to the outside, thereby manufacturing the medical mesh assembly according to the present invention.

In addition, a press, which is not shown in the drawings, may be provided for adhering the fixed member 20 to the mesh. Seats are formed at a position of the press corresponding to the position of the hook member 30 provided at the fixed member 2, and a welded portion is provided between the adjacent seats. The fixed member 20 is located at the mesh 10 and is pressurized and welded using the press so that the fixed member 20 can adhere to the mesh 10. In such a case, the fixed member is welded in a dot type for each section rather than being entirely welded, so that flexibility of the mesh 10 to which the fixed member 20 is connected can maintained, thereby increasing convenience for use. In addition, during the process for welding the fixed member 20 to the mesh 10 using the press, the press may melt the fixed member 20 or the mesh 10 or both using heat so that the fixed member 20 and the mesh can be firmly welded.

More specifically, in the processing step (200), the groove 21 is exactly formed at the upper part or the lower part or both of the fixed member (20) using a cutting tool such as a knife and the like so that the hook member 30 can be naturally formed. In such a case, the hook member 30, namely, the flat portion 23 in which the protrusions 30' are not formed, may be formed on a side of the fixed member 20 so as to facilitate insertion into a human body. Furthermore, in such a case, the hook member 30 may be prevented from being damaged, warped, or the like which may be caused when the fixed member 20 at which the hook member is formed adheres to the mesh 10, so that working availability can be improved.

Figure 8:
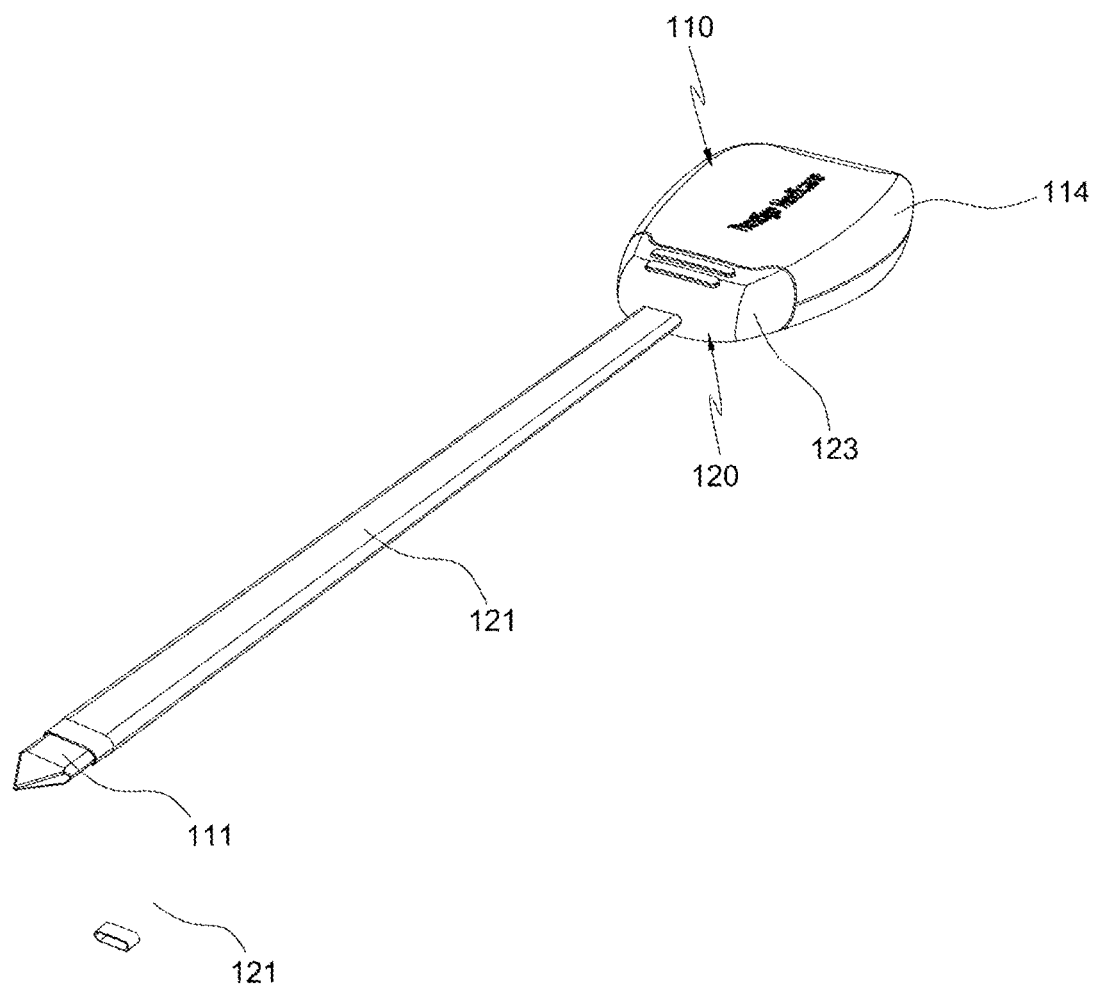
FIG. 8 is a perspective view of an insertion mechanism according to the present invention.
Figure 9:
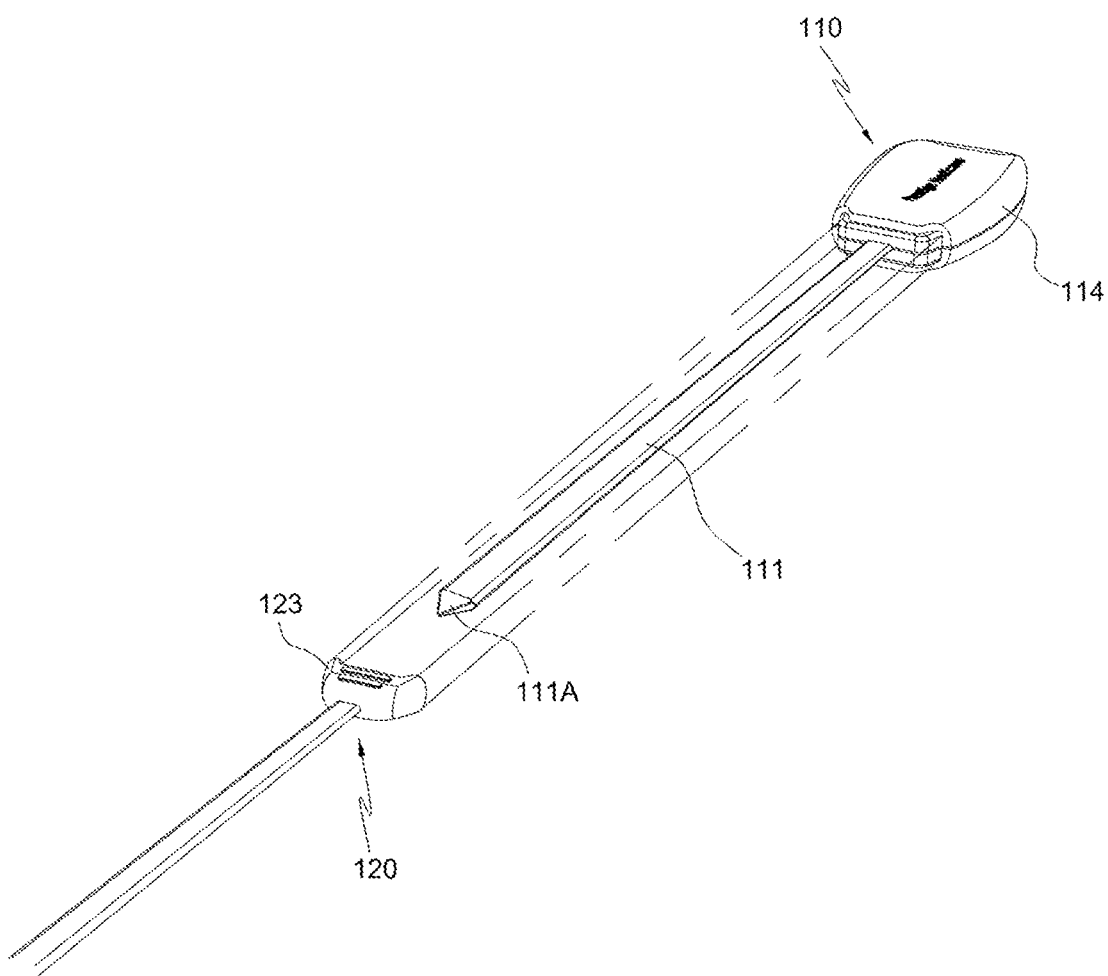
FIG. 9 is an exploded perspective view of the insertion mechanism according to the present invention.
Figure 10A:
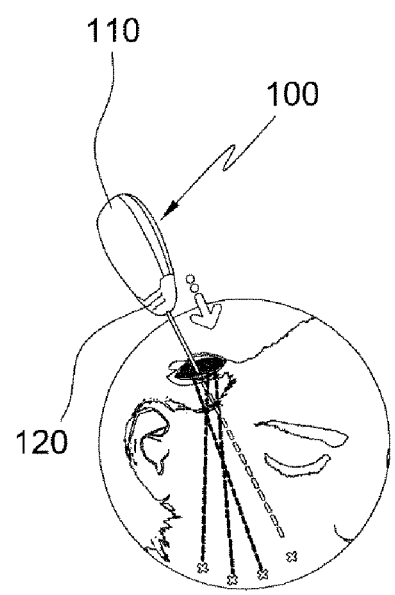
FIGS. 10A to 10D are views showing a first method for implementing a mesh assembly using the insertion mechanism according to the present invention.
Figure 10B:
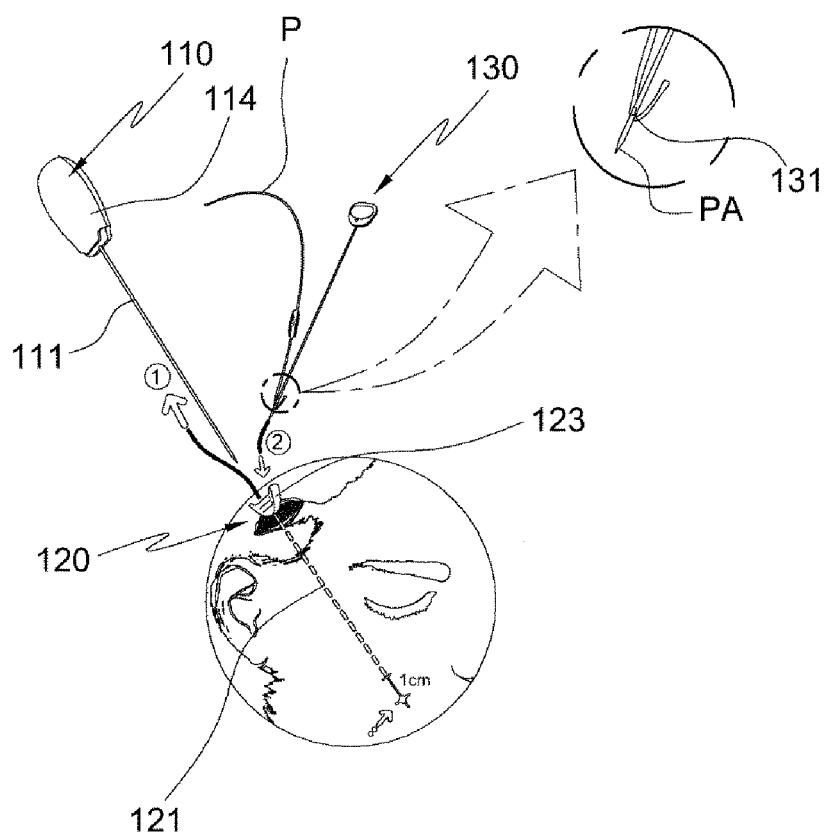
Figure 10C:
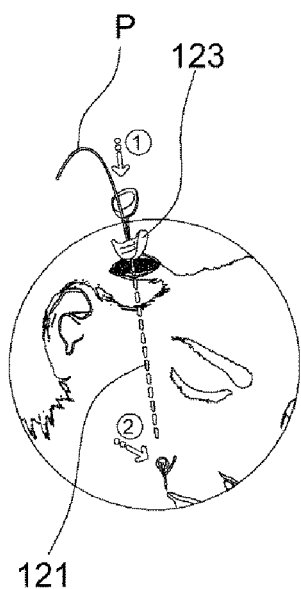
Figure 10D:
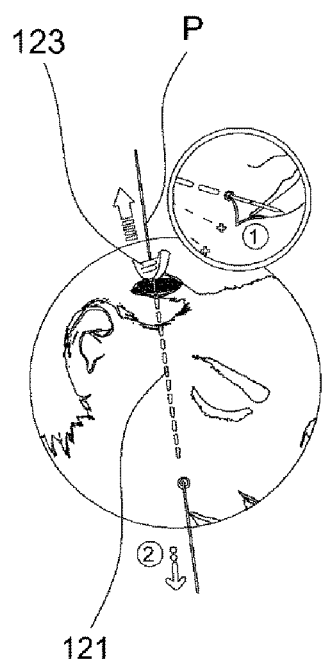

As illustrated in FIGS. 8 and 9, the mesh assembly according to the present invention may further include an insertion tool 100 adopted to insert the mesh assembly P into a soft tissue.

The insertion tool 100 includes a trocar 110 and a cannula that are inserted into the soft tissue, and a needle 130.

In detail, the trocar 110 includes an insertion portion 111 inserted into the soft tissue, and a handle portion 114 connected to the insertion portion 111. The insertion portion 111 of the trocar 110 further includes an inputting part 111A having a sharply formed end so as to pass through the soft tissue, and a passage is formed so that the mesh assembly P can be inserted to pass through the soft tissue via the insertion part 111A.

In order to conduct the insertion of the mesh assembly P smoothly, the cannula 120 is further provided so as to maintain the passage in the soft tissue. The cannula 120 includes: a through portion 121 in which the insertion portion 111 of the trocar 110 is interpolated; a bonding portion 123 formed at the through portion 121 and connected to the handle portion 114 of the trocar 110. Accordingly, when the trocar 110 to which the cannula 120 is connected is inserted into the soft tissue and is then pulled therefrom, the cannula 120 remains in the soft tissue so that the mesh assembly P can be easily inserted.

In such a case, in order for the inputting part 111A of the trocar 110 to protrude, the insertion portion 111 of the trocar 110 is formed longer than the through portion 121 of the cannula 120 so that the inputting part 111A of the trocar 110 is exposed to the end of the through portion 121 so as to easily pass through the soft tissue.

As illustrated in FIGS. 10A to 10D, the process for conducting a procedure using the insertion tool 100 will be described in detail as follows.

First, the trocar 110 to which the cannula 120 is connected is inserted into the soft tissue targeted for the procedure, and the trocar is then removed in a state of being inserted. In this case, the cannula 120 is located in the soft tissue so as to facilitate insertion of the mesh assembly P.

The mesh assembly P is put into the cannula 120 inserted into the soft tissue. In such a case, the needle 130 to which the mesh assembly P is connected is inserted into the cannula 120. An end PA of the needle 130 is sharply formed so that the end PA of the needle passing though the cannula 120 can bind the mesh assembly P to the soft tissue. The end PA of the needle may be more sharply formed than the end 111A of the trocar 110.

In addition, in order for the mesh assembly P to be connected to the needle 130, a coupling hole 131 is further formed at the end of the needle 130. The end of the needle 130 is caught by the coupling hole 131, and the needle 130 passes though the cannula 120 so that the mesh assembly P can be positioned in the cannula 120. Furthermore, the mesh assembly P may be positioned to protrude about 1 cm by passing through the cannula 120. However, this may be variously changed according to a procedure method and position.

In the case where the mesh assembly P is provided at a position corresponding to a part targeted for the procedure, the needle 130 and the cannula 120 are removed so that only the mesh assembly P can remain in the soft tissue.

Accordingly, the mesh assembly P may be more easily and conveniently inserted by the insertion tool 100 in the soft tissue so that time for the procedure can be reduced and the procedure can be simply and accurately conducted.

Figure 11:
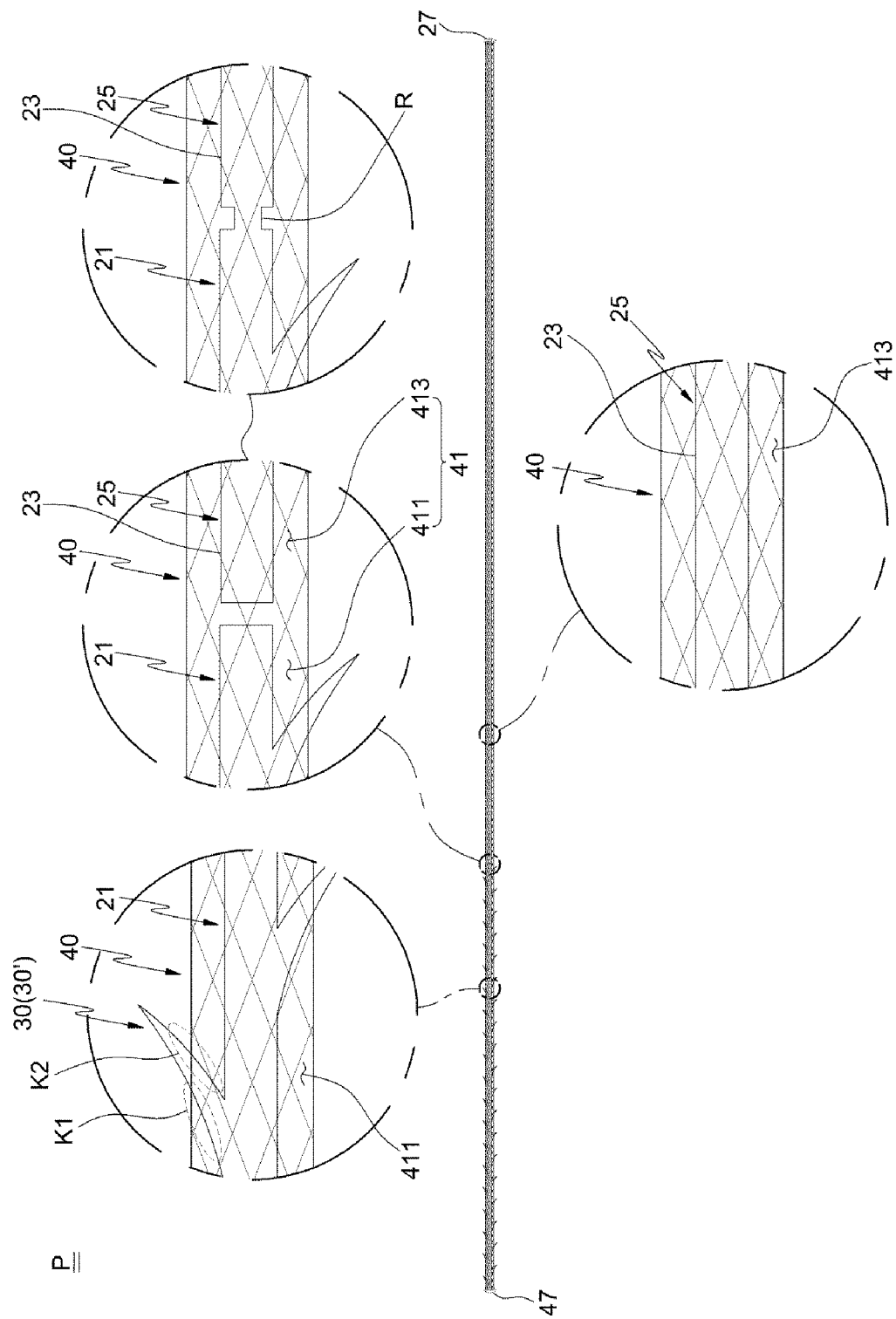
FIG. 11 is a side view of a mesh assembly according to a sixth embodiment of the present invention.
Figure 12:
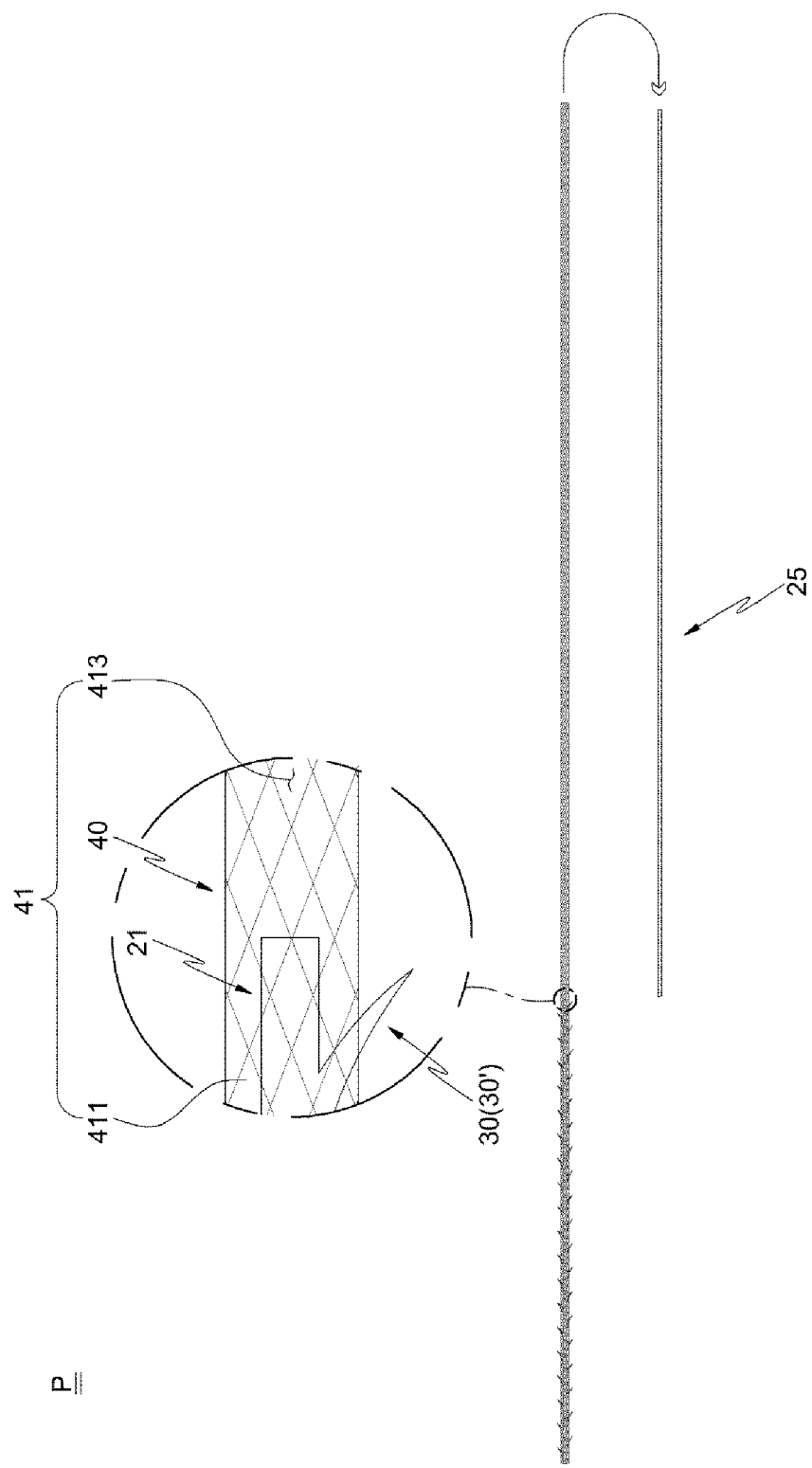
FIG. 12 is a view for implementing the mesh assembly according to the sixth embodiment of the present invention.
Figure 13:
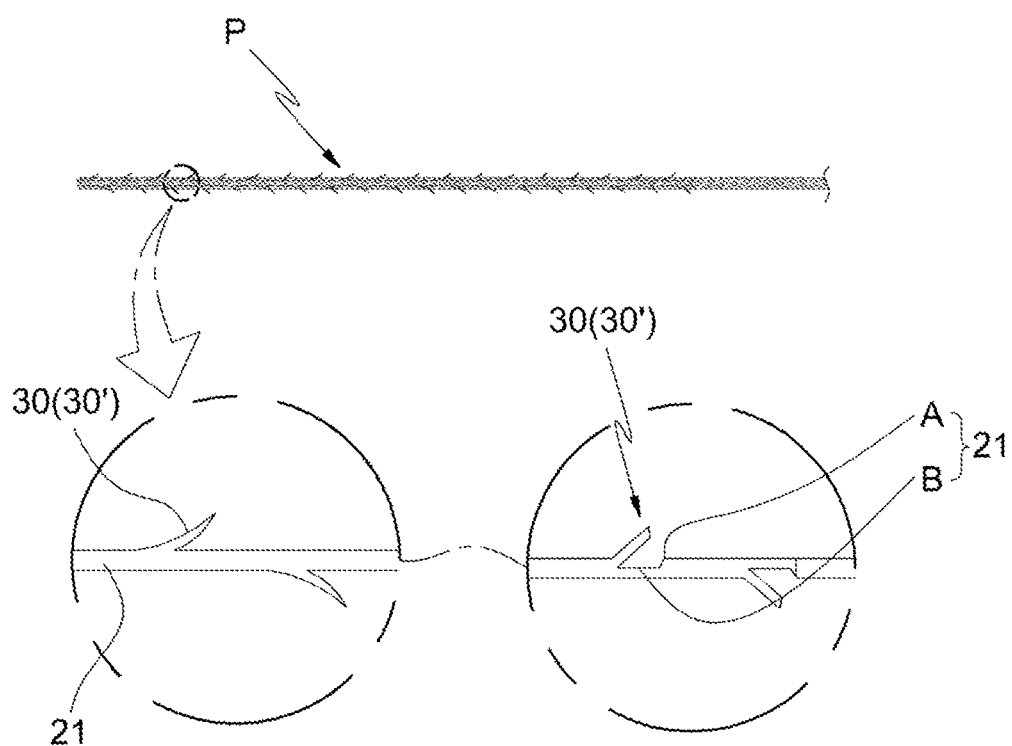
FIG. 13 is an enlarged view of the mesh assembly according to the sixth embodiment of the present invention.

First, as shown in the sixth embodiment illustrated in FIGS. 11 to 13, the mesh assembly P according to the present invention includes: a first thread 21 having the hook member 30; a second thread 25 positioned at a rear end of the first thread 21 and having the flat portion 23 rather than the hook member 30; and the mesh 40 formed to surround both the first thread 21 and the second thread 25 by forming a space portion 41 in which both the first thread 21 and the second thread 25 are interpolated.

In such a case, the space portion 41 may be divided into a first space part 411 in which the first thread 21 is interpolated, and a second space part 413 in which the second thread 25 is interpolated.

More specifically, the mesh 40 is made of a material that is harmless to humans and functions to lift the loose folds of skin in sagging and wrinkly skin tissues. The mesh may have a mesh structure so as to uniformly support the tissues by increasing a contact area with the tissues. The mesh 40 will be described in detail greater later.

The mesh assembly P according to the present invention includes the first thread 21 and the second thread 25 and is configured such that the hook member 30 is formed on an outer surface of the first thread 21, and the second thread 25 is positioned at the rear end of the first thread 21.

In detail, the first thread 21 is interpolated in the first space part 411, the second thread 25 is interpolated in the second space part 413, and the hook member 30 is formed on the outer circumferential surface of the first thread 21. In addition, the hook member 30 is composed of the plurality of protrusions 30' formed on the outer surface of the first thread 21. The protrusions 30' protrude to be oblique from the first thread 21 to one direction.

As illustrated in FIG. 11, when the first thread 21 is positioned in the mesh 40, the protrusions 30' of the first thread 21 protrude to an opening of the mesh 40. In this case, an upper part K1 of the mesh in contact with the protrusion 30' functions to push the protrusion 30' so that the protrusion 30' does not protrude any further. A part K2 in contact with a lower part of the protrusion 30' functions to support a bottom of the protrusion 30' to lift the protrusion 30' so that the protrusion 30' can protrude to the outside of the mesh 40.

Furthermore, when the first thread 21 is input into the mesh 40, the first thread 21 is inserted into the mesh from a right side of the mesh 40, and is then pulled in an opposite direction once again so that the protrusions 30' can protrude to the outside. At this time, in order for the protrusions 30' to protrude to the outside, after the first thread 21 has been input into the mesh 40, a left end of the first thread 21 and a left end of the mesh 40 should be fixed using a method such sealing or the like, and the first thread 21 should be pulled in the opposite direction.

The mesh assembly P according to the present invention has the mesh 40 interpolated in sagging skin or wrinkled skin or in a soft tissue for the purpose of beauty and is adopted to restore the sagging skin or wrinkled skin of human tissues.

More specifically, the mesh 40 has the first space part 411 having a cylindrical shape in which the first thread 21 is interpolated, and the second space part 413 in which the second thread is interpolated.

That is, the mesh 40 has a fixed volume therein due to the first space part 411 and the second space part 413. Thanks to the volume formed as such, a procedure for restoring or lifting the sagging skin and the wrinkled skin is carried out by adjusting the volume to be appropriate for the sagging skin and wrinkled skin.

Since the hook member 30 is provided so as to protrude to the outside according to nets provided at the mesh 40, an absorptive force with the soft tissue is increased so that the mesh assembly can be accurately fixed to a part targeted for the procedure.

Furthermore, since the mesh is formed in a cylindrical shape, it is effective to restore the elasticity of skin due to a tissue ingrowth phenomenon (which means that a tissue grows gradually in the mesh).

In addition, as illustrated in an alternate long and short dash line, the first thread 21 and the second thread 25 may be spaced apart from each other. However, an extension portion R having a diameter smaller than a diameter of the first thread 21 and the second thread 25 may be provided between the first thread 21 and the second thread 25 so as to connect the first thread and the second thread.

Accordingly, when the second thread 25 is separated from the first thread 21, the extension portion R having the small diameter is easily cut. Due to this, the second thread 25 may be easily separated from the first thread 21. Such a configuration is effective to prevent the second thread 25 from being lost and to further improve convenience of the procedure.

Figure 14:
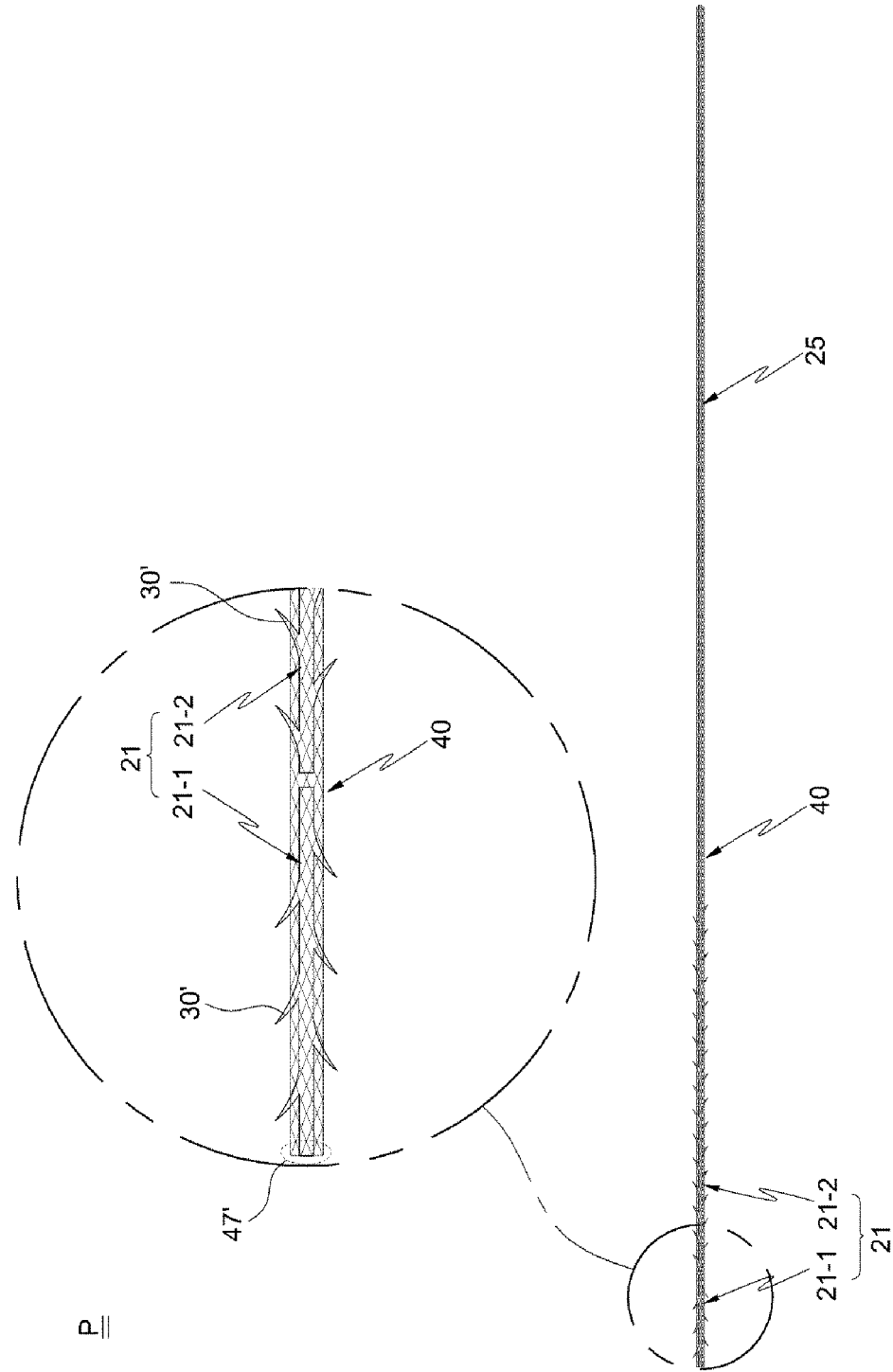
FIG. 14 illustrates a mesh assembly according to a seventh embodiment of the present invention.

FIG. 14 illustrates a mesh assembly according to a seventh embodiment of the present invention. As illustrated in FIG. 14, the first thread 21 may be composed of a first 1-1 string 21-1 and a first 1-2 string 21-2. The protrusions 30' of the first 1-1 string 21-1 and the first 1-2 string 21-2 may be formed in opposite directions.

In such a case, for convenience, when the first thread 21 positioned at the left side of the mesh 40 is defined as the first 1-1 string 21-1, a left end of the first 1-1 string 21-1 and a left end 47' of the mesh 40 may be fixed using a fixing method such as sealing or the like. In addition, since the first thread 21 is composed of the first 1-1 string 21-1 and the first 1-2 string 21-2 having the different protrusion directions, an absorptive force with tissues can be increased.

Also, the first thread 21 is divided into the first 1-1 string 21-1 and the first 1-2 string (21-2) such that the protrusion direction of the first 1-1 string 21-1 is opposite to the protrusion direction of the first 1-2 string 21-2 so that the protrusions of the first 1-1 string and the first 1-2 string can diagonally protrude in the opposite directions (see FIG. 14). In the case where the left side of the first 1-1 string 21-1 is sealed with the mesh 40 using heat treatment or the like, although a sealed part is separated from a tissue, the first 1-1 string 21-1 may be firmly fixed to the mesh 40 thanks to the protrusions formed to diagonally protrude to the left side, so that the thread 10 and the mesh 40 can be prevented from being separated from each other.

Returning to FIGS. 11 to 13 again, the mesh assembly P according to the present invention further includes the second thread 25. The second thread 25 is positioned at a rear end of the first thread 21 (a front end being defined as a direction at which the first thread is inserted into a human tissue), and unlike the first thread 21, the flat portion 23 rather than the hook member 30 is formed on an outer surface of the second thread 25 so that the second thread can be separated from the second space part 413 of the mesh 40.

In detail, the mesh 40 includes the first space part 411 in which the first thread 21 is interpolated, and the second space part 413 in which the second thread 25 is interpolated. The second thread 25 is inserted into the second space part 413, and as a result, the second thread is positioned at the rear end of the first thread 21.

When the mesh 40 is inserted into the human tissue, the second thread 25 includes the flat portion 23 having no hook member 30 on its outer surface, namely, having no protrusions 30' so as to be separated from the second space part 413.

This is intended to prevent the mesh 40 from not being smoothly knotted by the second thread 25 when the mesh 40 is knotted after completion of the procedure. As the second thread 25 is removed, only the mesh 40 remains so that ductility can be increased, thereby firmly making a knot.

In such a case, in order to prevent the second thread 25 to be separated from the mesh 40 during insertion of the mesh assembly P, a fixing portion 27 to which the rear end of the second thread 25 and the rear end of the mesh 40 are fixed is formed. The fixing portion 27 may enable the rear end of the second thread 25 and the rear end of the mesh 40 to adhere each other using heating or the like.

In addition, the fixing portion 27 is cut and removed using scissors, a knife, or the like after the mesh assembly P has been inserted into the human tissue. The second thread from which the fixing portion 27 is removed may be freely separated from the second space part 413 of the mesh 40.

Furthermore, FIG. 16 relates to the insertion tool 100 used in the procedure for the mesh assembly P according to the present invention. More specifically, the insertion tool 100 includes the trocar 110 and the cannula 120 that are input in the soft tissue.

The trocar 110 may include: an insertion portion 111 input into the soft tissue; and a handle portion 114 connected to the insertion portion 111. The insertion portion 111 of the trocar 110 further includes an inputting part having a sharply formed end so as to pass through the soft tissue, and a passage is formed so that the mesh assembly P can be inserted to pass through the soft tissue via the insertion part.

In order to conduct the insertion of the mesh assembly P smoothly, the cannula 120 is further provided so as to maintain the passage in the soft tissue. The cannula 120 includes: the through portion 121 in which the insertion portion 111 of the trocar 110 is interpolated; the bonding portion 123 formed at the through portion 121 and connected to the handle portion 114 of the trocar 110. Accordingly, when the trocar 110 to which the cannula 120 is connected is inserted into the soft tissue and is then pulled therefrom, the cannula 120 remains in the soft tissue so that inputting of the mesh assembly P can be induced.

In such a case, in order for the inputting part of the trocar 110 to protrude, the insertion portion 111 of the trocar 110 is formed longer than the through portion 121 of the cannula 120 so that the inputting part of the trocar 110 is exposed to the end of the through portion 121 so as to easily pass through the soft tissue.

The procedure using the mesh assembly P according to the present invention, which is conducted by the insertion tool 100, will be hereinafter described in detail greater.

Figure 15:
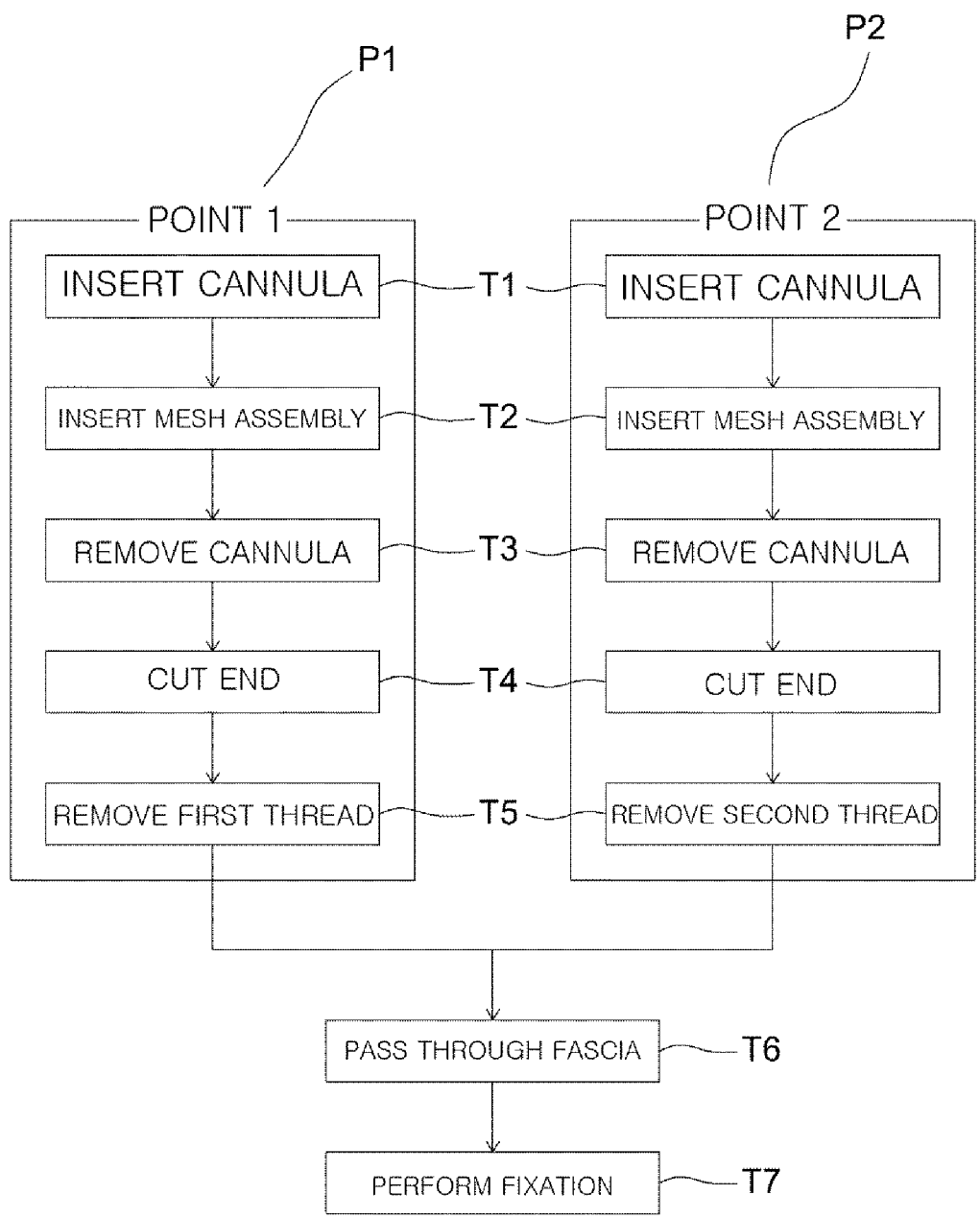
FIG. 15 is a block diagram showing a procedure using the mesh assembly according to the present invention.
Figure 17A:
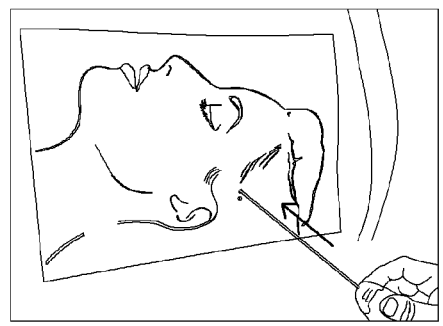
FIGS. 17A to 17L are schematic photo views showing a procedure using the mesh assembly according to the present invention.
Figure 17B:
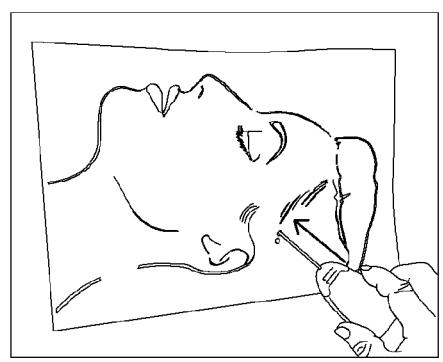
Figure 17C:
Figure 17D:
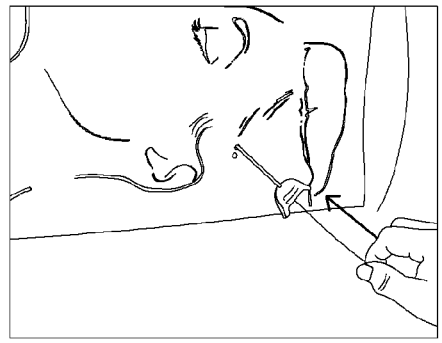
Figure 17E:
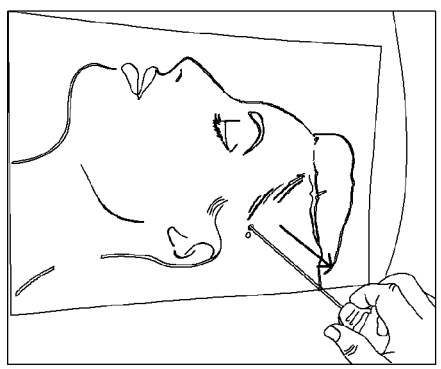
Figure 17F:
Figure 17G:
Figure 17H:
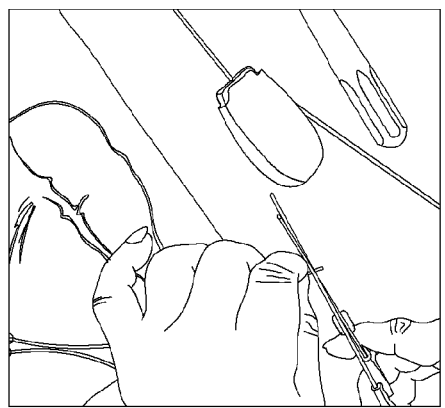
Figure 17I:
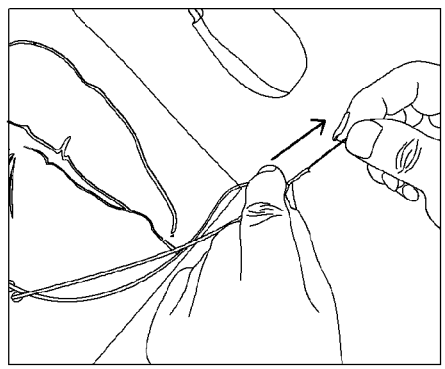
Figure 17J:
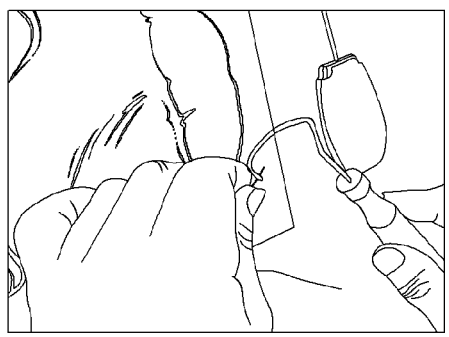
Figure 17K:
Figure 17L:

FIG. 15 illustrates a block diagram of a procedural method using the mesh assembly P, and FIGS. 17A to 17L are photo views showing procedure processes that are sequentially carried out.

First, a first process T1 is performed in such a manner that the insertion tool 100 is inserted into a position corresponding to a first point P1 targeted for the procedure, and the trocar 110 is removed so that the cannula 120 forms a passage.

A second process T2 is performed in such a manner that the mesh assembly P is input in the passage formed by the cannula 120 in the first process T1, and a third process T3 is performed in such a manner that an end of the mesh assembly P is supported and fixed in a state of the mesh assembly 40 being input, and the cannula 120 is then removed.

In addition, the mesh assembly P is also input in a second point P2 adjacent to the first point P1 in the same manner as in the first point P1 so that the mesh assembly P is configured to be inserted into the first point P1 and the second point P2.

A fourth process T4 is performed in such a manner that the fixing portion 27 arranged at a rear end of the mesh assembly P configured as described above is cut so that the mesh 40 and the second thread 25 are freely separated from the second space part 413, wherein the cutting is conducted using a knife, scissors, or the like.

Subsequently, a fifth process T5 is performed in such a manner that the second thread 25 is removed from the second space part 413 by causing the second thread to protrude in a state of holding the mesh 40 so that only the first thread 21 can be interpolated in the mesh assembly P provided at the first point P1 and the second point P2.

In addition, the first to fifth processes T1, T2, T3, T4, and T5 are performed in the same manners at the first point P1 and the second point P2.

After these processes have been completed, a sixth process T6 is performed in such a manner that the ends of the mesh assembly P are knotted, and in such a case, the mesh 40 of the first point P1 is moved to the second point P2 by a conventionally used fascia penetration tool so that the mesh assembly P can be firmly fixed to the human tissue because the mesh is moved by passing through the fascia. Since the fascia penetration tool is a conventionally used and publicly known tool, the description thereof is omitted.

As a result, through a seventh process T7 in which two mesh assemblies P protruding to the second point P2 are tied, thereby making knots, the procedure is completed. Thus, wrinkles or sinking sites in the human tissue can be restored by forming a volume in the wrinkles or sinking sites.

Although the embodiments of the present invention have been described for illustrative purposes based on the mesh assembly having specific shapes and constitutions with reference to the accompanying drawings, those skilled in the art will appreciate that various modifications, additions and substitutions are possible, without departing from the scope and spirit of the invention as disclosed in the accompanying claims. The modifications, additions and substitutions should be construed as falling within the scope of the protection of the present invention.

What is claimed is:

1. A mesh assembly, comprising:
a first thread having a hook member on an outer surface thereof;
a second thread having no hook member and positioned at a rear end of the first thread; and
a mesh having a space portion in which both the first thread and the second thread are interpolated, and formed to surround both the first thread and the second thread,
wherein the space portion comprises a first space part in which the first thread is interpolated, and a second space part in which the second thread is interpolated;
wherein a rear end of the second thread and a rear end of the mesh are fixed to each other; and
wherein a fixing portion, which may be cut, is formed so that the second thread is separated from the second space part by cutting.

2. The mesh assembly of claim 1, wherein the hook member of the first thread comprises protrusions protruding diagonally in one direction.

3. The mesh assembly of claim 2, wherein the hook member protrudes to an outside of the mesh.

4. The mesh assembly of claim 3, wherein the hook member of the first thread is caught by the mesh so as to prevent the first thread from being separated from the mesh.

5. The mesh assembly of claim 4, wherein the first thread has a plurality of grooves, each of the grooves comprising a diagonal line portion formed diagonal to the first thread, and a straight line portion extending to an end of the diagonal line portion and formed in a lengthwise direction of the first thread.

6. The mesh assembly of claim 3, wherein the first thread has a plurality of grooves, each of the grooves comprising a diagonal line portion formed diagonal to the first thread, and a straight line portion extending to an end of the diagonal line portion and formed in a lengthwise direction of the first thread.

7. The mesh assembly of claim 2, wherein the first thread has a plurality of grooves, each of the grooves comprising a diagonal line portion formed diagonal to the first thread, and a straight line portion extending to an end of the diagonal line portion and formed in a lengthwise direction of the first thread.

8. The mesh assembly of claim 1, wherein an outer surface of the second thread is composed of a flat portion.

9. The mesh assembly of claim 8, wherein the first thread has a plurality of grooves, each of the grooves comprising a diagonal line portion formed diagonal to the first thread, and a straight line portion extending to an end of the diagonal line portion and formed in a lengthwise direction of the first thread.

10. The mesh assembly of claim 1, wherein the mesh is in a cylindrical shape.

* * * * *